(12) United States Patent
Zabotkin et al.

(10) Patent No.: US 12,678,241 B2
(45) Date of Patent: Jul. 14, 2026

(54) PULLEY SUPPORTS FOR END EFFECTOR WRISTS

(71) Applicant: Cilag GmbH International, Zug (CH)

(72) Inventors: Konstantin Zabotkin, Mason, OH (US); Pavel Shalakov, Blue Ash, OH (US); Andrew Crews, Cincinnati, OH (US); Joseph Mueller, South Lebanon, OH (US)

(73) Assignee: Cilag GmbH International, Zug (CH)

( * ) Notice: Subject to any disclaimer, the term of this patent is extended or adjusted under 35 U.S.C. 154(b) by 313 days.

(21) Appl. No.: 18/505,944

(22) Filed: Nov. 9, 2023

(65) Prior Publication Data

US 2025/0152263 A1 May 15, 2025

(51) Int. Cl.
*A61B 34/30* (2016.01)
*A61B 34/00* (2016.01)

(52) U.S. Cl.
CPC .............. *A61B 34/30* (2016.02); *A61B 34/71* (2016.02); *A61B 2034/305* (2016.02)

(58) Field of Classification Search
CPC ... A61B 34/30; A61B 34/71; A61B 2034/305; A61B 2034/306; A61B 34/37; A61B 17/29
See application file for complete search history.

(56) References Cited

U.S. PATENT DOCUMENTS

| | | | |
|---|---|---|---|
| 6,312,435 B1 * | 11/2001 | Wallace | ................. A61B 34/30 |
| | | | 606/130 |
| 11,160,601 B2 * | 11/2021 | Worrell | .............. A61B 18/1445 |

| | | | |
|---|---|---|---|
| 2015/0127045 A1 * | 5/2015 | Prestel | ................... A61B 34/30 |
| | | | 606/208 |
| 2015/0209965 A1 * | 7/2015 | Low | ......................... B25J 17/02 |
| | | | 901/29 |
| 2016/0374766 A1 | 12/2016 | Schuh | |
| 2017/0080580 A1 * | 3/2017 | Kishi | ................. A61B 18/1492 |
| 2017/0165010 A1 * | 6/2017 | Chaplin | ................. A61B 34/30 |
| 2017/0172553 A1 | 6/2017 | Chaplin et al. | |
| 2021/0369372 A1 * | 12/2021 | Schuh | .................... B25J 9/1045 |
| 2023/0293160 A1 * | 9/2023 | Waterbury | ....... A61B 17/00234 |
| | | | 606/1 |

FOREIGN PATENT DOCUMENTS

| | | |
|---|---|---|
| EP | 3845155 A1 | 7/2021 |
| EP | 3900641 A1 | 10/2021 |
| WO | 2023128665 A1 | 7/2023 |

OTHER PUBLICATIONS

International Search Report from corresponding PCT Application No. PCT/IB2024/061098 mailed Apr. 1, 2025.

* cited by examiner

*Primary Examiner* — Andrew Restaino
(74) *Attorney, Agent, or Firm* — Vorys, Sater, Seymour and Pease LLP

(57) ABSTRACT

A surgical tool includes a drive housing having an elongate shaft extending therefrom, an end effector arranged at a distal end of the shaft and including opposing first and second jaws, and a wrist interposing the shaft and the end effector. The wrist includes a clevis, a pulley support mounted to the clevis at an axle having a pivot axis extending through the axle, and a pulley rotatably mounted to the pulley support and rotatable about a rotation axis that is non-collinear with the pivot axis. The surgical tool further includes a plurality of drive cables extending from the drive housing, wherein one of the plurality of drive cables is routed through the wrist and engages the pulley.

20 Claims, 13 Drawing Sheets

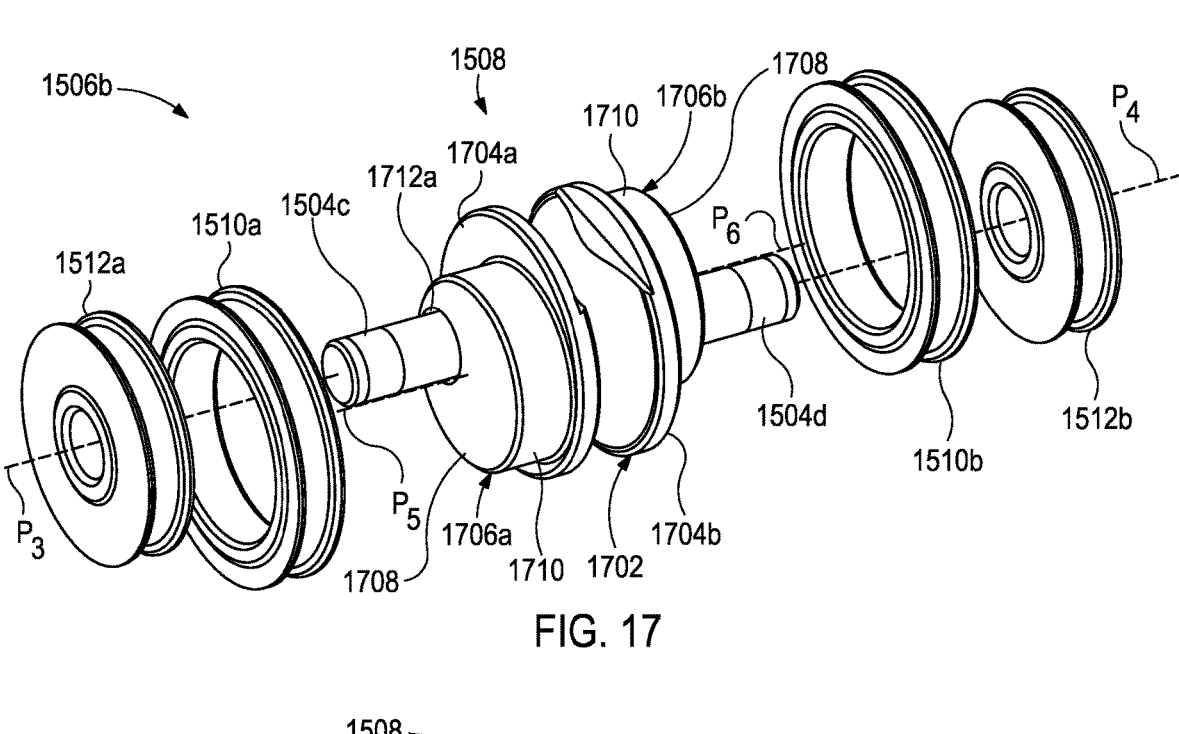
FIG. 17
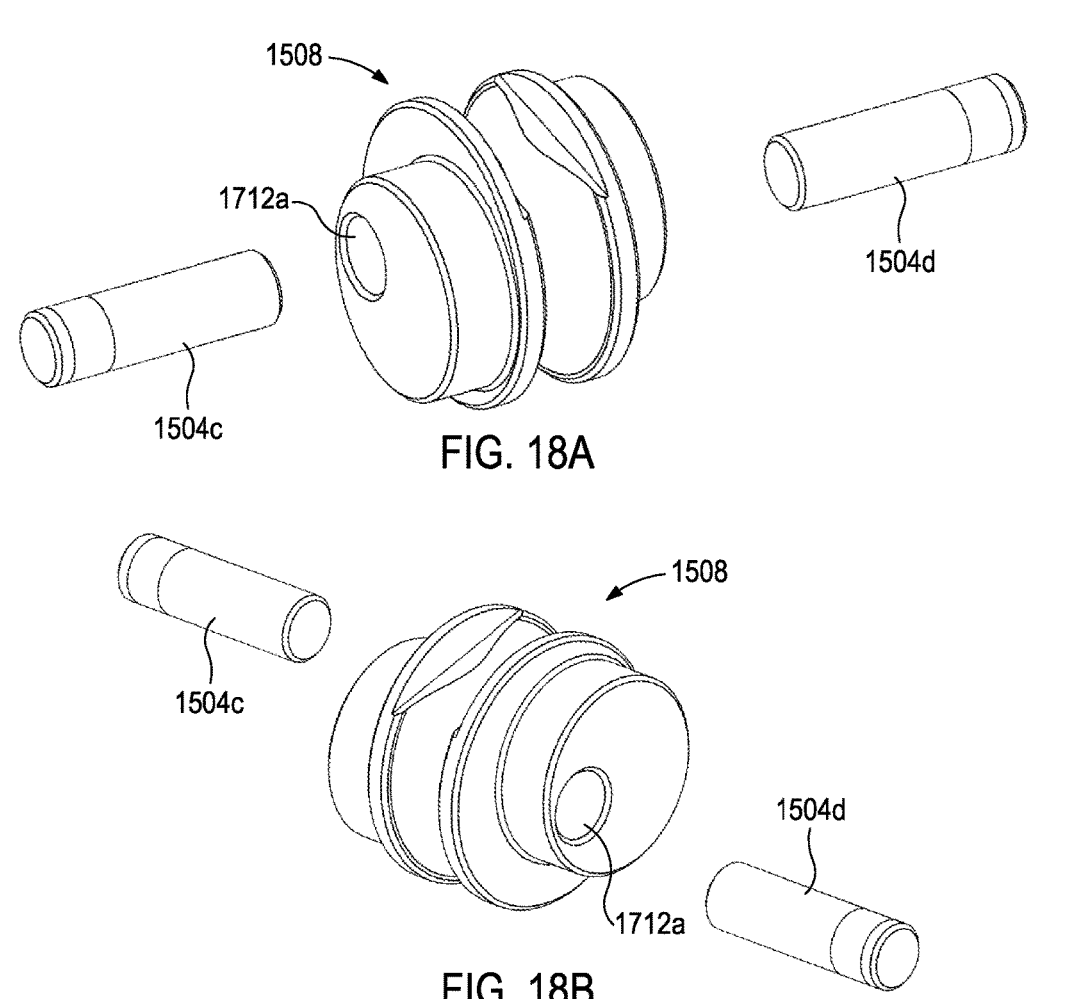
FIG. 18A
FIG. 18B

PULLEY SUPPORTS FOR END EFFECTOR WRISTS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

In cable-driven MIS instruments, wrist architecture is vital in helping to reduce cable tension while enhancing mechanical advantage. Wrist architecture can also be a source of high strain if small pulleys with large fleet angles are incorporated. Improved wrist architecture is always desirable to reduce costs and improve tool useful life.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 17 is a partially exploded isometric view of the second set of pulleys of FIG. 16, according to one or more embodiments.

FIGS. 18A and 18B are exploded, isometric left and right views of the pulley support and the third and fourth axles, according to one or more embodiments.

DETAILED DESCRIPTION

The present disclosure generally describes robotic surgical tools and, more specifically, surgical tool end effectors and wrists with pulley supports to rotatably mount cable pulleys The embodiments disclosed herein describe a surgical tool that can include a drive housing having an elongate shaft extending therefrom, an end effector arranged at a distal end of the shaft and including opposing first and second jaws, and a wrist interposing the shaft and the end effector. The wrist may include a clevis, a pulley support mounted to the clevis at an axle having a pivot axis extending through the axle, and a pulley rotatably mounted to the pulley support and rotatable about a rotation axis that is non-collinear with (or distinct from) the pivot axis. A plurality of drive cables may extend from the drive housing and one of the plurality of drive cables is routed through the wrist and engages the pulley.

In other embodiments, the wrist may include a clevis and a pulley support mounted to the clevis, where the pulley support includes a substrate having opposing front and back faces, a first bushing provided on the front face, and a second bushing provided on the back face. The wrist may further include a first pulley rotatably mounted to the pulley support at the first bushing, and a second pulley rotatably mounted to the pulley support at the second bushing. A plurality of drive cables may extend from the drive housing to the end effector and may include a first drive cable engageable with the first pulley and a second drive cable engageable with the second pulley.

Figure 1:
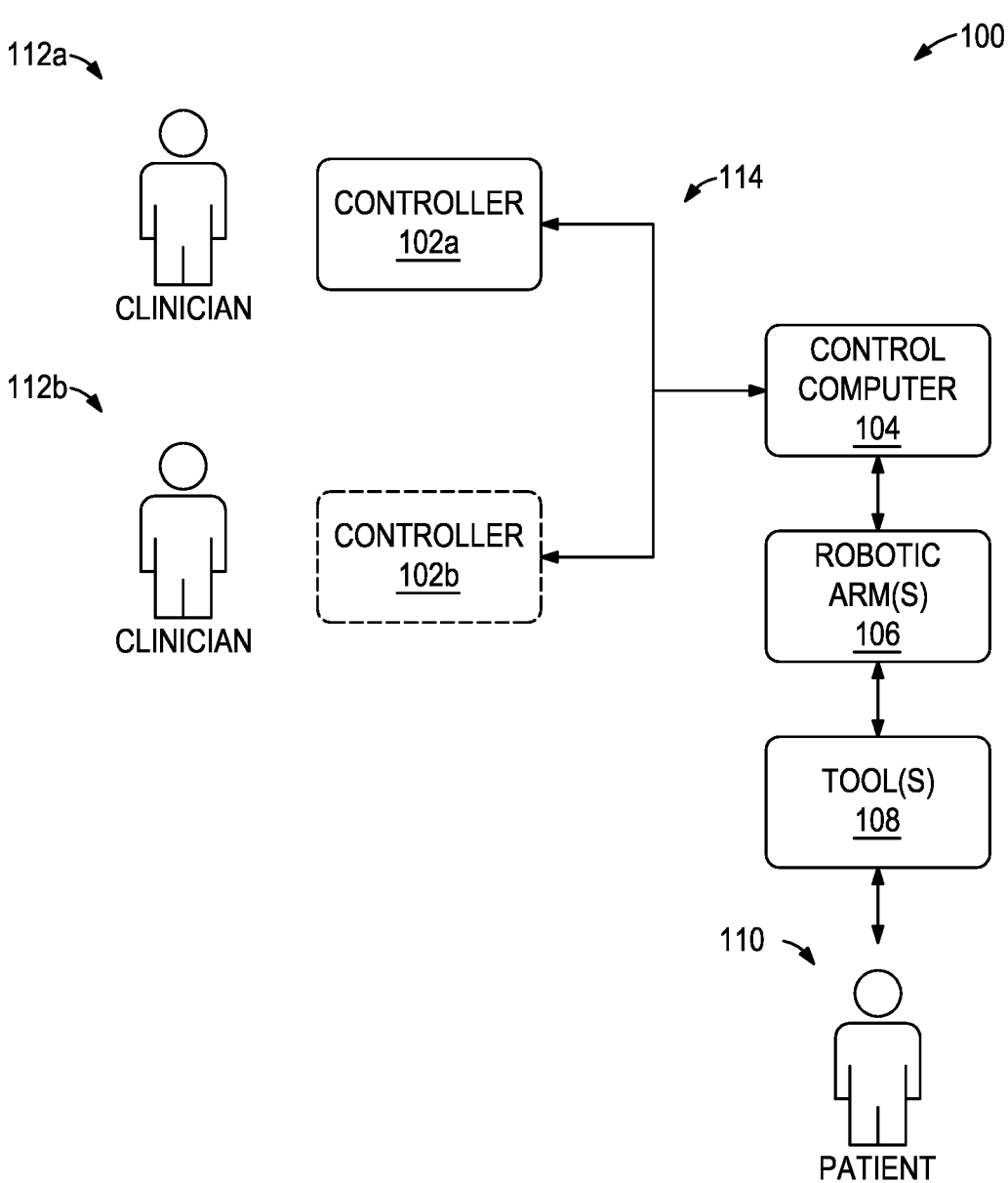
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
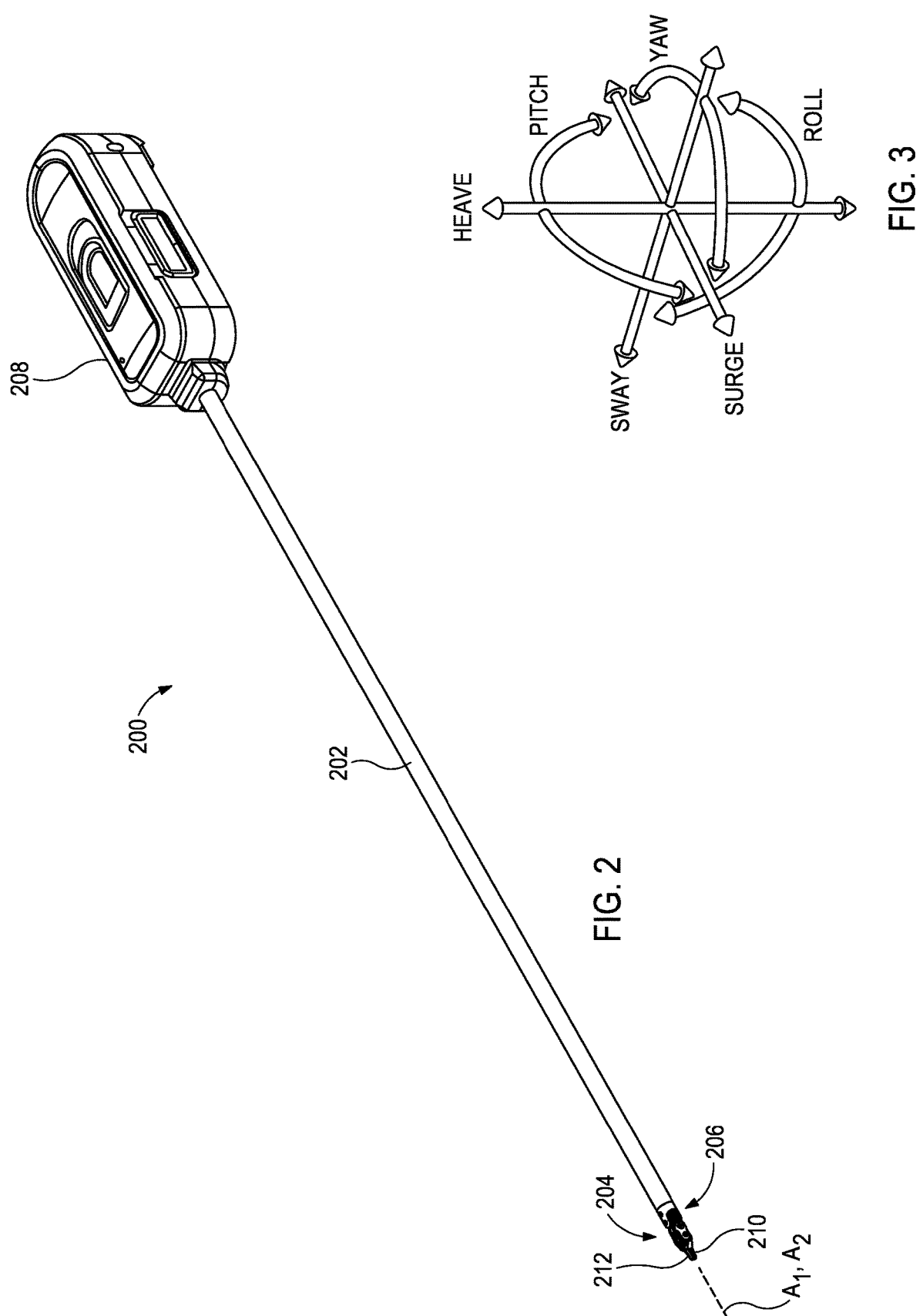
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the drive housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the drive housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the drive housing 208 is configured to control rotational movement of the shaft 202 about the longitudinal axis $A_1$.

The shaft 202 is an elongate member extending distally from the drive housing 208 and has at least one lumen extending therethrough along its axial length. In some embodiments, the shaft 202 may be fixed to the drive housing 208, but could alternatively be rotatably mounted to the drive housing 208 to allow the shaft 202 to rotate about the longitudinal axis $A_1$. In yet other embodiments, the shaft 202 may be releasably coupled to the drive housing 208, which may allow a single housing 208 to be adaptable to various shafts having different end effectors.

The end effector 204 can exhibit a variety of sizes, shapes, and configurations. In the illustrated embodiment, the end effector 204 comprises a combination tissue grasper or "needle driver" that includes opposing first and second jaws 210, 212 configured to move (articulate) between open and closed positions. As will be appreciated, however, the opposing jaws 210, 212 may alternatively form part of other types of end effectors such as, but not limited to, surgical scissors, a clip applier, a babcock including a pair of opposed grasping jaws, bipolar jaws (e.g., bipolar Maryland grasper, forceps, a fenestrated grasper, etc.), etc. One or both of the jaws 210, 212 may be configured to pivot to transition the end effector 204 between the open and closed positions.

FIG. 3 illustrates the potential degrees of freedom in which the wrist 206 may be able to articulate (pivot) and thereby correspondingly move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Selectively actuating the drive cables, for example, can cause the jaws 210, 212 to move (transition) between open and closed positions. Moreover, selectively actuating the drive cables can also cause the end effector 204 to articulate (move) between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

Figure 4A:
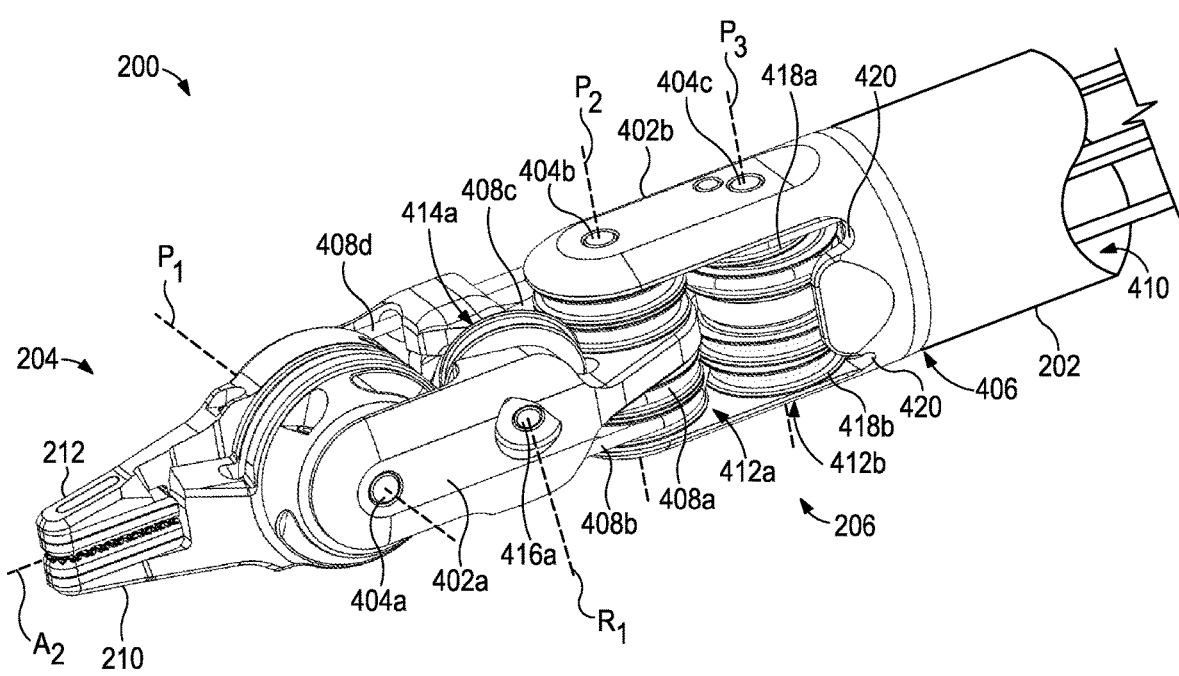
FIGS. 4A and 4B are enlarged isometric views of the distal end of the surgical tool of FIG. 2 from opposing vantage points, according to one or more embodiments.
Figure 4B:
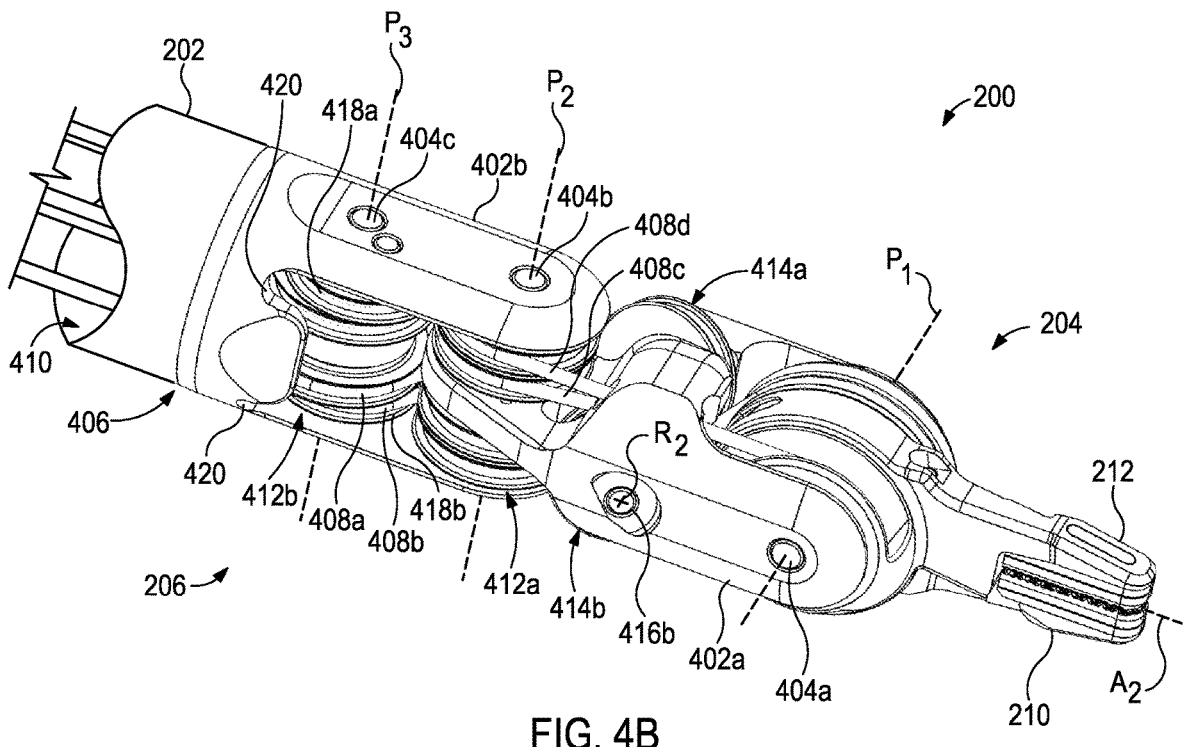

FIGS. 4A and 4B are enlarged, isometric views of the distal end of the surgical tool 200, according to one or more embodiments. More specifically, FIG. 4A is an enlarged, isometric view of the end effector 204 and the wrist 206 from a right side perspective, and FIG. 4B is an enlarged, isometric view of the end effector 204 and the wrist 206 from a left side perspective. The wrist 206 operatively couples the end effector 204 to the shaft 202 (or a shaft adapter interposing the distal end of the shaft 202 and the wrist 206). To accomplish this, the wrist 206 includes a distal clevis 402a and a proximal clevis 402b. The jaws 210, 212 are rotatably mounted to the distal clevis 402a at a first axle 404a, the distal clevis 402a is rotatably mounted to the proximal clevis 402b at a second axle 404b, and the proximal clevis 402b is operatively coupled to a distal end 406 of the shaft 202.

The wrist 206 provides a first pivot axis $P_1$ that extends through the first axle 404a and a second pivot axis $P_2$ that extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "pitch" (up and down) articulation of the end effector 204, and movement about the second pivot axis $P_2$ provides "yaw" (left and right) articulation of the end effector 204. The jaws 210, 212 are mounted at the first pivot axis $P_1$, which allows the jaws 210, 212 to pivot relative to each other to open and close the end effector 204 or alternatively pivot in tandem to articulate the orientation of the end effector 204.

A plurality of drive cables, shown as drive cables 408a, 408b, 408c, and 408d, extend longitudinally within a lumen 410 defined by the shaft 202 and pass through the wrist 206 to be operatively coupled to the end effector 204. The lumen 410 can be a single lumen, as illustrated, or can alternatively comprise a plurality of independent lumens, where each lumen receives one or more of the drive cables 408a-d.

The drive cables 408a-d may form part of the cable driven motion system mentioned above and housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 408a-d can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof. While four drive cables 408a-d are depicted in FIG. 4A-4B, more or less than four may be employed, without departing from the scope of the disclosure.

The drive cables 408a-d extend proximally from the end effector 204 to the drive housing 208 (FIG. 2) where they are operatively coupled to various actuation mechanisms or devices housed (contained) therein to facilitate longitudinal movement (translation) of the drive cables 408a-d within the lumen 410. Selective actuation of one or all of the drive cables 408a-d causes the end effector 204 to articulate (pivot) relative to the shaft 202. More specifically, selective actuation causes a corresponding drive cable 408a-d to translate longitudinally within the lumen 410 and thereby causes articulating or operating movement of the end effector 204. One or more drive cables 408a-d, for example, may be actuated to cause the end effector 204 to articulate (e.g., both of the jaws 210, 212 moved in a same direction), to cause the end effector 204 to open (e.g., one or both of the jaws 210, 212 move away from the other), or to cause the end effector 204 to close (e.g., one or both of the jaws 210, 212 move toward the other).

Moving the drive cables 408a-d can be accomplished in a variety of ways, such as by triggering an associated actuator or mechanism operatively coupled to or housed within the drive housing 208 (FIG. 2). Moving a given drive cable 408a-d constitutes applying tension (i.e., pull force) to the given drive cable 408a-d in a proximal direction, which causes the given drive cable 408a-d to translate and thereby cause the end effector 204 to move (articulate) relative to the shaft 202.

The wrist 206 includes a first set of pulleys 412a and a second set of pulleys 412b, each configured to interact with and redirect the drive cables 408a-d as they pass through the wrist 206 to be operatively coupled to the end effector 204. The first set of pulleys 412a is rotatably mounted to the proximal clevis 402b at the second axle 404b and the second set of pulleys 412b is also rotatably mounted to the proximal clevis 402b but at a third axle 404c located proximal to the second axle 404b. A third pivot axis $P_3$ extends through the third axle 404c and is parallel to the second pivot axis $P_2$. The first and second sets of pulleys 412a,b cooperatively redirect the drive cables 408a-d through an "S" shaped pathway (alternately referred to as an "S-curve" or "S-bend") before being operatively coupled to the end effector 204 at the jaws 210, 212. The drive cables 408a-d may be operatively coupled to the jaws 210, 212 via a variety of ways such as, but not limited to, crimps, welds, mechanical fasteners, or any combination thereof.

In at least one embodiment, one pair of drive cables 408a-d is operatively coupled to each jaw 210, 212 and configured to "antagonistically" operate the corresponding jaw 210, 212. In the illustrated embodiment, for example, the first and second drive cables 408a,b are coupled to (terminate at) the first jaw 210, and the third and fourth drive cables 408c,d are coupled to (terminate at) the second jaw 212. Actuation of the first drive cable 408a acts on and pivots the first jaw 210 about the first pivot axis $P_1$ toward the closed position. In contrast, actuation of the second drive cable 408b acts on and pivots the first jaw 210 about the first pivot axis $P_1$ toward the open position. Similarly, actuation of the third drive cable 408c pivots the second jaw 212 about the first pivot axis $P_1$ toward the closed position, while actuation of the fourth drive cable 408d pivots the second jaw 212 about the first pivot axis $P_1$ toward the open position. Accordingly, the first and third drive cables 408a,c may alternatively be referred to herein as "closure" cables, and the second and fourth drive cables 408b,c may alternatively be referred to herein as "open" cables. Simultaneous actuation of the closure cables 408a,c will cause the jaws 210, 212 to close, and simultaneous actuation of the open cables 408b,d will cause the jaws 210, 212 to open.

The drive cables 408a-d may be characterized or otherwise referred to as "antagonistic" cables that cooperatively (yet antagonistically) operate to cause relative or tandem movement of the first and second jaws 210, 212. More particularly, when the first drive cable 408a is actuated (moved), the second drive cable 408b naturally follows since it is also coupled to the first jaw 210, and vice versa. Similarly, when the third drive cable 408c is actuated, the fourth drive cable 408d naturally follows since it is also coupled to the second jaw 210, and vice versa.

Accordingly, coordinated actuation of the open and closure cables 408a-d may cause the jaws 210, 212 to open or close, and also articulate the end effector 204 about one or both of the first and second pivot axes $P_1$, $P_2$. Consequently, the end effector 204 can articulate with multiple degrees of freedom, e.g., a degree of freedom by articulating about the first pivot axis $P_1$ and another degree of freedom by articulating about the second pivot axis $P_2$. The wrist 206 in this embodiment is pivotable about the second pivot axis $P_2$ in a single plane, e.g., in one of pitch and yaw, and the end effector 204 is pivotable about the first pivot axis $P_1$ in a single, different plane, e.g., the other of pitch and yaw.

In some embodiments, the wrist 206 may further include a first redirect pulley 414a and a second redirect pulley 414b (FIG. 4B). The redirect pulleys 414a,b may be rotatably mounted to the distal clevis 402a and arranged to axially interpose the first set of pulleys 412a and the jaws 210, 212. The first redirect pulley 414a may be configured to receive the first drive cable 408a (i.e., the "first closure cable") from the first set of pulleys 412a and redirect the first closure cable 408a to the first jaw 210. Similarly, the second redirect pulley 414b may be configured to receive the third drive cable 408c (i.e., the "second closure cable") from the first set of pulleys 412a and redirect the second closure cable 408c to the second jaw 212. Redirecting the first and second closure cables 408a,c from the first set of pulleys 412a to the jaws 210, 212 using the redirect pulleys 414a,b helps reduce or entirely eliminate the fleet angle of the first and second closure cables 408a,c as they are received by the first and second jaws 210, 212, respectively.

As illustrated, the first redirect pulley 414a is rotatably mounted to the distal clevis 402a at a first redirect axle 416a (FIG. 4A), and the second redirect pulley 414b is rotatably mounted to the distal clevis 402a at a second redirect axle 416b (FIG. 4B). Moreover, the first redirect pulley 414a is rotatable about a first redirect pivot axis $R_1$ (FIG. 4A), and the second redirect pulley 414b is rotatable about a second redirect pivot axis $R_2$ (FIG. 4B). The first and second redirect axes $R_1$, $R_2$ are angularly offset from each of the longitudinal axis $A_2$ of the end effector 204, the first pivot axis $P_1$, and the second pivot axis $P_2$. In some embodiments, for example, the first and second redirect axes $R_1$, $R_2$ may be angularly offset from the first pivot axis $P_1$ by around 45° and simultaneously angularly offset from the second pivot axis $P_2$ by around 45°. In other embodiments, however, the first and second redirect axes $R_1$, $R_2$ may be angularly offset from the first and second pivot axes $P_1$, $P_2$ by more or less than 45°, without departing from the scope of the disclosure.

According to embodiments of the present disclosure, the surgical tool 200 (and other surgical tools described hereinafter) may include one or more monolithic (single part) pulley supports used to mount one or more of the pulleys included in the wrist; e.g., the first or second sets of pulleys 412a,b or the redirect pulleys 414a,b. The presently described pulley supports may be designed to rotatably support the wrist pulleys in different orientations and locations relative to each other using one or two pins (axles). One advantage of the pulley support embodiments described herein is that such designs produce a space-efficient support to mount pulleys that can be as large as possible within the confines of the envelope defined by the wrist 206. Moreover, the pulley supports promote increased mechanical advantage with lower cable loads, which leads to extended life of the drive cables 408a-d.

In the illustrated embodiment, the surgical tool 200 includes first and second pulley supports (not visible) mounted to the third axle 404c and otherwise forming part of the second set of pulleys 412b. As will be described in more detail below, first and second "low force" pulleys 418a and 418b included in the second set of pulleys 412b may be rotatably mounted to the pulley supports and configured to receive and reroute the open cables 408b,d in the wrist 206. The configuration and geometry of the pulley supports shift the rotation axis of the low force pulleys 418a,b to be eccentric to the third pivot axis $P_3$, as discussed below. This also allows the size (e.g., diameter) of each low force pulley 418a,b to be increased, which increases the life of the open cables 408b,d by reducing the bending stress of the cable material.

In some embodiments, to accommodate for the increased size of the low force pulleys 418a,b, the proximal clevis 402b may define reliefs or slots 420 laterally aligned with the low force pulleys 418a,b. In at least one embodiment, for example, one or both of the low force pulleys 418a,b may extend laterally outward and into the adjacent slot 420.

Figures 5A, 5B:
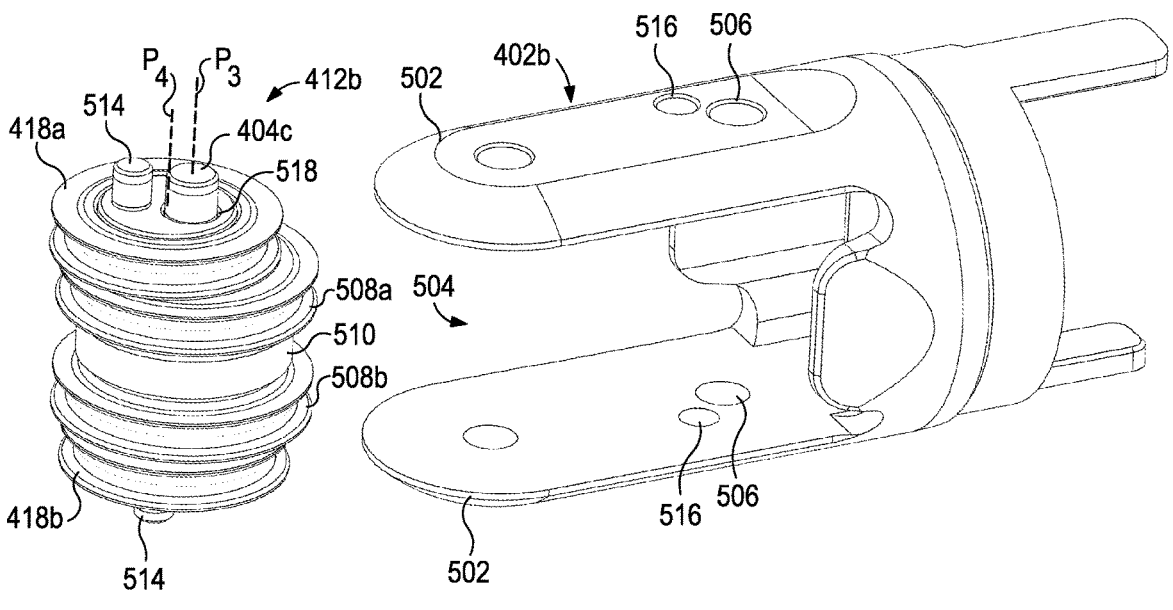
FIGS. 5A and 5B are partially exploded top and bottom isometric views, respectively, of the proximal clevis and the second set of pulleys of FIGS. 4A-4B, according to one or more embodiments.

FIGS. 5A and 5B are partially exploded, top and bottom isometric views, respectively, of the proximal clevis 402b and the second set of pulleys 412b, according to one or more embodiments. In particular, the second set of pulleys 412b is shown exploded from the proximal clevis 402b to enable a more complete view of the assembly.

As illustrated, the proximal clevis 402b includes first and second distally extending arms 502 that extend in corresponding horizontal, parallel planes. A gap 504 is provided between the arms 502 to accommodate the second set of pulleys 412b. While not shown, the gap 504 may also be configured to accommodate the first set of pulleys 412a (FIGS. 4A-4B). The second set of pulleys 412b may be rotatably mounted to the distally extending arms 502 at the third axle 404c, which is receivable within corresponding apertures 506 defined in the proximal clevis 402b and, more particularly, in the distally extending arms 502.

As illustrated, the second set of pulleys 412b includes the first and second outer or "low force" pulleys 418a,b and first and second inner or "high force" pulleys 508a,b. The low force pulleys 418a,b are arranged at or near the opposing ends of the third axle 404c, and the high force pulleys 508a,b interpose the low force pulleys 418a,b. In at least one embodiment, a spacer 510 may be included in the second set of pulleys 412b and axially interposes the high force pulleys 508a,b. The closure cables 408a,c (FIGS. 4A-4B) may be configured to be routed through the wrist 206 (FIGS. 4A-4B) on the high force pulleys 508a,b, and the open cables 408b,d (FIGS. 4A-4B) may be configured to be routed through the wrist 206 on the low force pulleys 418a,b.

As illustrated, the second set of pulleys 412b includes a first pulley support 512a and a second pulley support 512b, where the first low force pulley 418a is rotatably mounted to the first pulley support 512a, and the second low force pulley 418b is rotatably mounted to the second pulley support 512b. Each pulley support 512a,b provides a cylindrical axle boss 514, alternately referred to as a low force bushing orientation feature, extending laterally outward from the body of the corresponding pulley support 512a,b. Each cylindrical axle boss 514 may be receivable within a corresponding boss aperture 516 defined in the proximal clevis 402b and, more particularly in the distally extending arms 502. The cylindrical axle bosses 514 may be configured to properly orient ("clock") the pulley support 512a,b on the proximal clevis 402b, and thereby properly orient the corresponding low force pulley 418a,b within the wrist 206. In some embodiments, the cylindrical axle boss 514 may be integrated in the proximal clevis 402b. In such embodiments, a low force bushing may be used as an integral part of the proximal clevis 402b and may establish a pivot axis $P_4$ for the low force pulley 418a while providing an extended support for the third axle 404c, which establishes the third pivot axis $P_3$.

Each pulley support 512a,b may also provide and otherwise define a support aperture 518 configured to receive the opposing ends of the third axle 404c. The low force pulleys 418a,b rotate on the corresponding pulley support 512a,b about a rotation axis $P_4$ of the corresponding pulley support 512a,b. As illustrated, the rotation axis $P_4$ is non-collinear with (distinct from) the pivot axis $P_3$ extending through the third axle 404c. More specifically, the rotation axis $P_4$ is parallel but eccentric to the pivot axis $P_3$. Consequently, in operation each low force pulley 418a,b rotates on the corresponding pulley support 512a,b eccentric to the pivot axis $P_3$, and thus also eccentric to the high force pulleys 508a,b.

Figures 6A, 6B, 7:
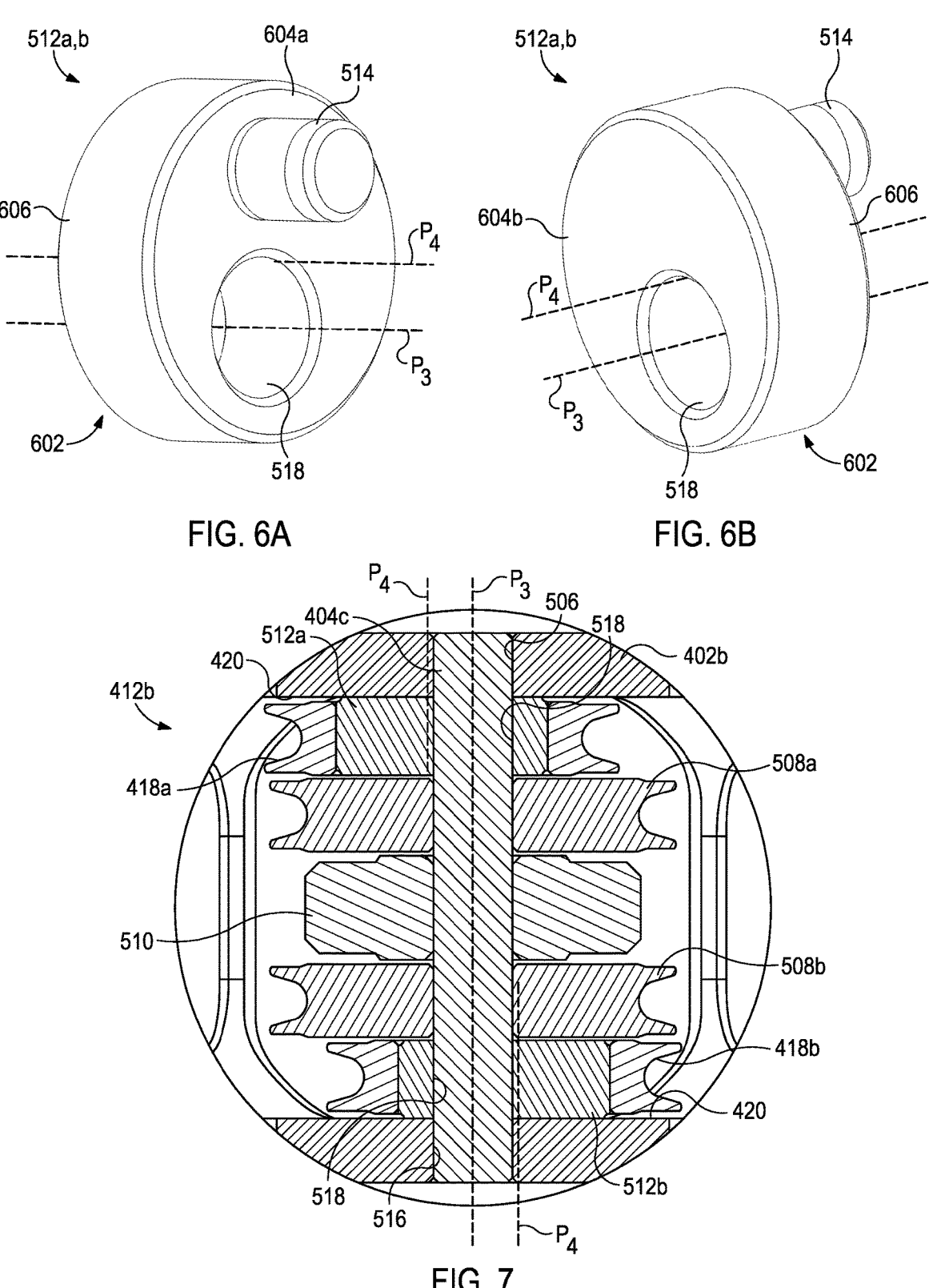
FIGS. 6A and 6B are isometric front and back views respectively, of an example of the pulley supports of FIGS. 5A-5B, according to one or more embodiments.
FIG. 7 is a cross-sectional side view of the second set of pulleys of FIGS. 5A-5B taken through the third pivot axis $P_3$, according to one or more embodiments.

FIGS. 6A and 6B are isometric front and back views respectively, of an example of the pulley supports 512a,b, according to one or more embodiments. As illustrated, the pulley supports 512a,b provide a generally cylindrical body 602 having a circular cross-section. The body 602 provides a front face 604a, a back face 604b opposite the front face 604a, and a smooth and circular side wall 606 extending between the front and back faces 604a,b. The low force pulleys 418a,b (FIGS. 5A-5B) may be configured to be rotatably mounted to the pulley supports 512a,b on the side wall 606. Moreover, as illustrated, the cylindrical axle boss 514 extends laterally outward from the front face 604a of the body 602.

As mentioned above, each pulley support 512a,b defines the support aperture 518, which extends through the body 602 between the front and back faces 604a,b. The support aperture 518 is configured to receive the opposing ends of the third axle 404c (FIGS. 5A-5B) and, accordingly, the third pivot axis $P_3$ extends through the center of the support aperture 518. The rotation axis $P_4$ of the pulley support 512a,b, however, is non-collinear (e.g., eccentric, distinct) to the pivot axis $P_3$, thus allowing the low force pulleys (FIGS. 5A-5B) to rotate on the pulley support 512a,b eccentric to the third pivot axis $P_3$.

FIG. 7 is a cross-sectional side view of the second set of pulleys 412b taken through the third pivot axis $P_3$, according to one or more embodiments. As illustrated, the second set of pulleys 412b is rotatably mounted to the distal clevis 402b at the third axle 404c, which is receivable within the corresponding apertures 506. The high force pulleys 508a,b and the spacer 510 are concentrically mounted to the third axle 404c, and the high force pulleys 508a,b rotate about the third pivot axis $P_3$ during operation. The first and second pulley supports 512a,b are also mounted to the third axle 404c at corresponding support apertures 518, and the low force pulleys 418a,b are rotatably mounted to each pulley support 512a,b, respectively. The low force pulleys 418a,b rotate on the corresponding pulley support 512a,b about the rotation axis $P_4$ of the corresponding pulley support 512a,b, where the rotation axis $P_4$ is non-collinear (e.g., eccentric, distinct) to the third pivot axis $P_3$. As a result, each low force pulley 418a,b rotates eccentric to the pivot axis $P_3$ and also eccentric to the high force pulleys 508a,b during operation.

Accordingly, each pulley support 512a,b comprises a single (monolithic) part designed to rotatably support the low force pulleys 418a,b at a different rotation axis $P_4$ relative to the third pivot axis $P_3$ about which the high force pulleys 508a,b rotate. This may prove advantageous in allowing for a smaller size (e.g., small diameter) for the third axle 404c, which could minimize frictional losses. Moreover, this also allows for larger low force pulleys 418a,b since the pulley supports 512a,b offset the rotation axis $P_4$, thus allowing the use of the wall thickness of the proximal clevis 402b for space gain. As illustrated, the larger diameter low force pulley 418a,b may extend at least partially into the slots 420 defined in the sidewall of the proximal clevis 402b.

Figure 8A:
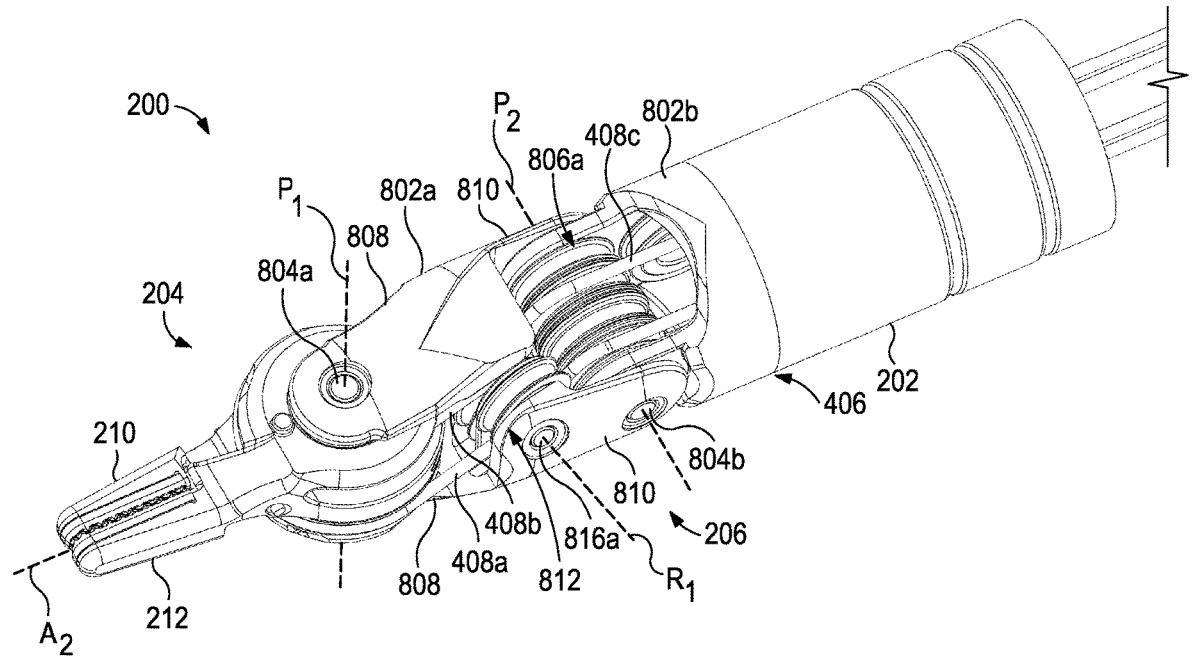
FIGS. 8A and 8B are enlarged, isometric views of another example of the distal end of the surgical tool of FIG. 2, according to one or more additional embodiments.
Figure 8B:
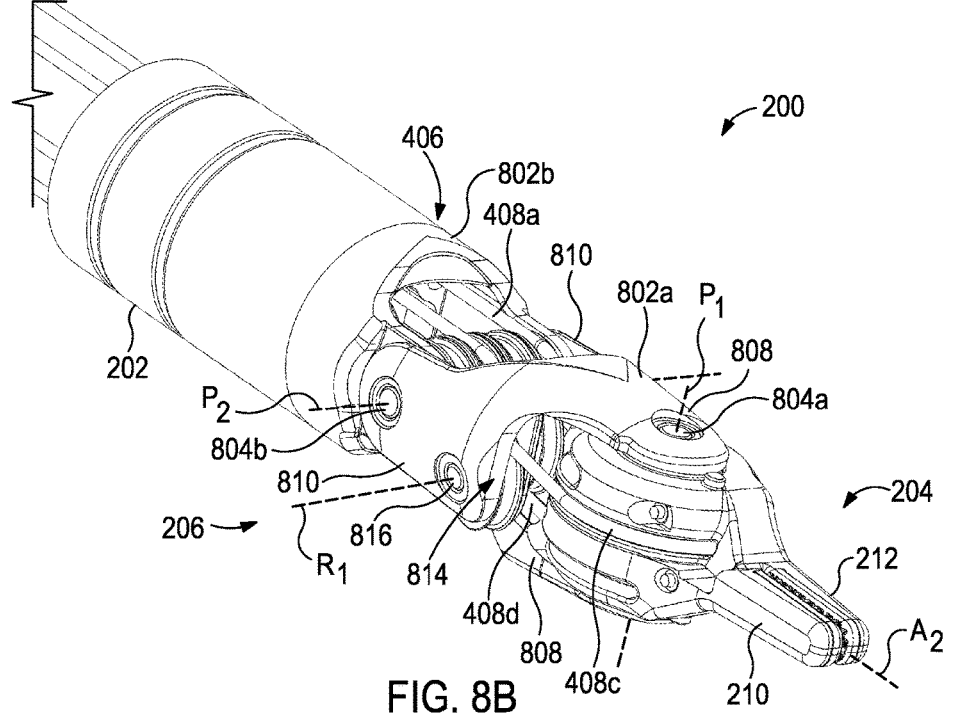

FIGS. 8A and 8B are enlarged, isometric views of another example of the distal end of the surgical tool 200, according to one or more additional embodiments. More specifically, FIGS. 8A-8B are enlarged left and right isometric views of alternative examples of the end effector 204 and the wrist 206. The embodiment shown in FIGS. 8A-8B may be substantially similar to the embodiment of FIGS. 4A-4B, and therefore may be best understood with reference thereto, where like numerals will represent like components not described again in detail. As illustrated, the wrist 206 operatively couples the end effector 204 to the shaft 202 (or a shaft adapter interposing the distal end of the shaft 202 and the wrist 206). Moreover, the wrist 206 includes a distal clevis 802a and a proximal clevis 802b. The jaws 210, 212 are rotatably mounted to the distal clevis 802a at a first axle 804a, the distal clevis 802a is rotatably mounted to the proximal clevis 802b at a second axle 804b, and the proximal clevis 802b is operatively coupled to the distal end 406 of the shaft 202. The first pivot axis $P_1$ extends through the first axle 804a and the second pivot axis $P_2$ extends through the second axle 804b.

The drive cables 408a-d pass through the wrist 206 and are operatively coupled to the end effector 204. In the illustrated embodiment, the drive cables pass 408a-d through at least a first set of pulleys 806a before reaching the end effector 204. The first set of pulleys 806a is rotatably mounted to the proximal clevis 802b at the second axle 804b, and the drive cables 408a-d may be operatively coupled to the jaws 210, 212 via a variety of ways such as, but not limited to, crimps, welds, mechanical fasteners, or any combination thereof. The first and second drive cables 408a,b are coupled to (terminate at) the first jaw 210, and the third and fourth drive cables 408c,d are coupled to (terminate at) the second jaw 212. As mentioned above, the first and third drive cables 408a,c are referred to herein as "closure" cables, and the second and fourth drive cables 408b,c are referred to herein as "open" cables.

As illustrated, the distal clevis 802a includes first and second distally extending arms 808, and the jaws 210, 212 are arranged between (interpose) the distally extending arms 808 in a gap defined between the arms 808. Each end of the first axle 804a extends through or is otherwise mounted to a corresponding one of the distally extending arms 808, and the jaws 210, 212 are rotatably mounted to the first axle 804.

The distal clevis 802a further includes first and second proximally extending arms 810 that extend in the opposite direction as the distally extending arms 808. In the illustrated embodiment, the distally extending arms 808 extend in corresponding horizontal, parallel planes, and the proximally extending arms 810 extend in corresponding vertical, parallel planes, where the vertical and horizontal planes are 90° offset from each other. The first set of pulleys 806a is rotatably mounted to the proximally extending arms 810 at the second axle 804b, which extends through corresponding apertures defined in the proximally extending arms 810.

The wrist 206 further includes one or more first redirect pulleys 812 (FIG. 8A) and one or more second redirect pulleys 814 (FIG. 8B). In the illustrated embodiment, there are two first redirect pulleys 812 and two second redirect pulleys 814, but less than two could be included, without departing from the scope of the disclosure. The redirect pulleys 812, 814 may be rotatably mounted to the distal clevis 802a and arranged to axially interpose the first set of pulleys 806a and the jaws 210, 212. The first redirect pulleys 812 may be configured to receive the first and second drive cables 408a,b from the first set of pulleys 806a and redirect the drive cables 408a,b to the first and second jaws 210, respectively. Similarly, the second redirect pulleys 814 may be configured to receive the third and fourth drive cables 408c,b from the first set of pulleys 806a and redirect the drive cable 408c,d to the second and first jaws 212, 210 respectively. Redirecting the drive cables 408a-d from the first set of pulleys 806a to the jaws 210, 212 using the redirect pulleys 812, 814 helps reduce or entirely eliminate the fleet angle of the drive cables 408a-d as they are received by the first and second jaws 210, 212.

In the illustrated embodiment, the redirect pulleys 812, 814 are mounted to first and second pulley supports (not visible), respectively, mounted to the distal clevis 802a. As described in more detail below, the first and second pulley supports may be mounted to the distal clevis 802a at a redirect axle 816 that extends uninterrupted between lateral sides of the distal clevis 802a. A redirect pivot axis $R_1$ extends through the redirect axle 816 and may be angularly offset from each of the longitudinal axis $A_2$ of the end effector 204, the first pivot axis $P_1$, and the second pivot axis $P_2$. In some embodiments, for example, the redirect pivot axis $R_1$ may be angularly offset from the first pivot axis $P_1$ by around 45° and simultaneously angularly offset from the second pivot axis $P_2$ by around 45°. In other embodiments, however, the first and second redirect axes $R_1$, $R_2$ may be angularly offset from the first and second pivot axes $P_1$, $P_2$ by more or less than 45°, without departing from the scope of the disclosure. As described in more detail below, the first and second redirect pulleys 812, 814 are rotatably mounted to the first and second pulley supports, respectively, but are mounted at an angle offset from the redirect pivot axis $R_1$ such that their axis of rotation is also angularly offset from the redirect pivot axis $R_1$.

Figure 9A:
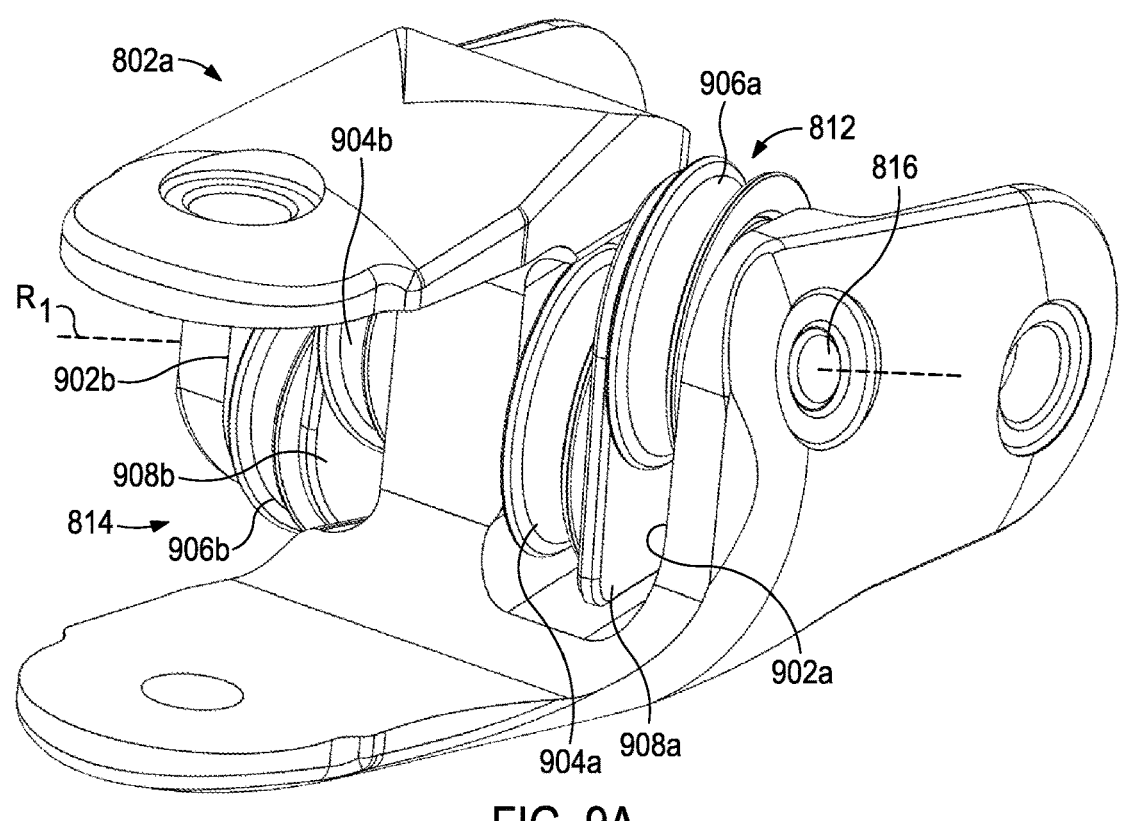
FIGS. 9A and 9B are isometric right and left views, respectively, of the distal clevis and the first and second redirect pulleys of FIGS. 8A-8B, according to one or more embodiments.
Figure 9B:
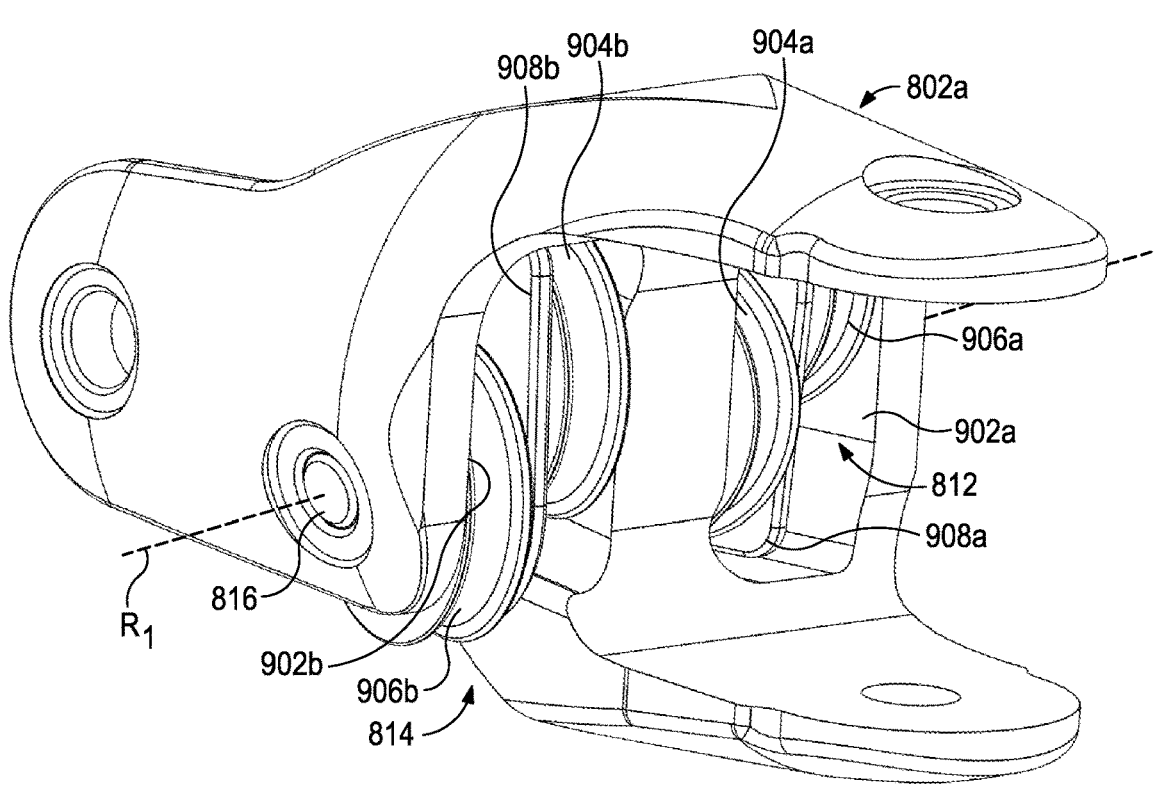

FIGS. 9A and 9B are isometric right and left views, respectively, of the distal clevis 802a and the first and second redirect pulleys 812, 814, according to one or more embodiments. In some embodiments, as illustrated, the distal clevis 802a may provide and otherwise define a first slot 902a configured to accommodate and otherwise receive the first redirect pulleys 812, and a second slot 902b configured to accommodate and otherwise receive the second redirect pulleys 814.

In the illustrated embodiment, the first redirect pulleys 812 include a first low force redirect pulley 904a and a first high force redirect pulley 906a, and the second redirect pulleys 812 include a second low force redirect pulley 904b and a second high force redirect pulley 906b. The first and second low force redirect pulleys 904a,b may be configured to redirect the open cables 408b,d (FIGS. 8A-8B) to the jaws 210, 212 (FIGS. 8A-8B), and the first and second high force redirect pulleys 906a,b may be configured to redirect the closure cables 408a,c (FIGS. 8A-8B) to the jaws 210, 212.

The first redirect pulleys 812 (i.e., the first low force and high force redirect pulleys 904a, 906a) are each rotatably mounted to a first pulley support 908a within the first slot 902a. The second redirect pulleys 814 (i.e., the second low force and high force redirect pulleys 904b, 906b) are each rotatably mounted to a second pulley support 908b within the second slot 902b. The first and second pulley supports 908a,b are mounted to the distal clevis 802a and, more particularly, mounted to the redirect axle 816 that extends through the distal clevis 802a along the redirect pivot axis $R_1$. The first and second redirect pulleys 812, 814 are rotatably mounted to the first and second pulley supports 908a,b, respectively, but rotate about axes that are angularly offset from the redirect pivot axis $R_1$.

Figures 10A, 10B, 11A, 11B:
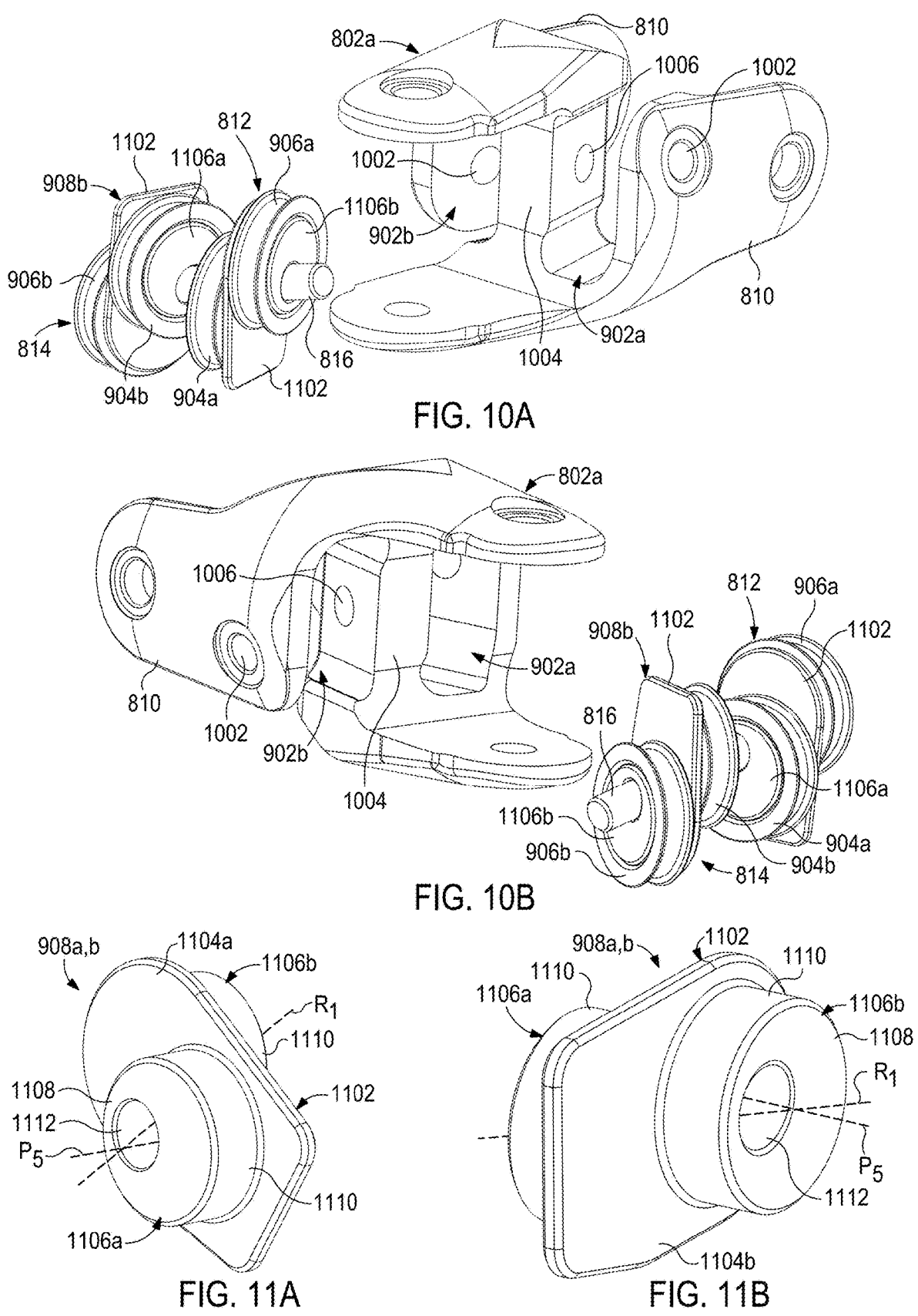
FIGS. 10A and 10B are right and left isometric exploded views, respectively, of the distal clevis and the first and second redirect pulleys of FIGS. 8A-8B, according to one or more embodiments
FIGS. 11A and 11B illustrate left and right isometric views, respectively, of an example pulley support, according to one or more embodiments.

FIGS. 10A and 10B are right and left isometric exploded views, respectively, of the distal clevis 802 and the first and second redirect pulleys 812, 814, according to one or more embodiments. As illustrated, the distal clevis 802a provides and otherwise defines opposing redirect axle apertures 1002 configured to receive the opposing ends of the redirect axle 816. More particularly, the redirect axle apertures 1002 may be defined in the proximally extending arms 810 of the distal clevis 802*a*. Moreover, the distal clevis 802 further provides a central support 1004, which defines a central aperture 1006 through which the redirect axle 816 also extends. The redirect axle 816 extends uninterrupted from one redirect axle aperture 1002, through the central aperture 1006, and terminating at the opposing redirect axle aperture 1002. The first and second slots 902*a,b* are defined laterally between the central support 1004 and the laterally adjacent proximally extending arms 810, respectively. As indicated above, the first slot 902*a* is configured to accommodate the first redirect pulleys 812 mounted to the first pulley support 908*a*, and the second slot 902*b* is configured to accommodate the second redirect pulleys 814 mounted to the second pulley support 908*b*.

Referring briefly to FIGS. 11A and 11B, illustrated are left and right isometric views, respectively, of an example pulley support 908*a,b*, according to one or more embodiments. The pulley support shown in FIGS. 11A-11B represents either pulley support 908*a,b*, which are substantially identical. As illustrated, the pulley support 908*a,b* provides a substrate 1102 having opposing front and back faces 1104*a* and 1104*b*. In the illustrated embodiment, the substrate 1102 is substantially planar. A first bushing 1106*a* extends from or is otherwise provided on the front face 1104*a* and extends away from the substrate 1102, and a second bushing 1106*b* extends from or is otherwise provided on the back face 1104*b* and extends away from the substrate 1102. As illustrated, each bushing 1106*a,b* provides a generally cylindrical body 1108 having a circular cross-section and a smooth and circular side wall 1110. The low and high force pulleys 904*a,b* and 906*a,b* (FIGS. 9A-9B) may be configured to be rotatably mounted to the pulley supports 908*a,b* on the corresponding side walls 1110. Each bushing 1106*a,b* allows the corresponding pulley 904*a,b* and 906*a,b* to rotate on the corresponding pulley support 908*a,b* about a rotation axis $P_5$.

As illustrated, the pulley support 908*a,b* includes a support aperture 1112 defined coaxially through the opposing bushings 1106*a,b* and extending uninterrupted through the entire pulley support 908*a,b*. The support apertures 1112 provided in each bushing 1106*a,b* are configured to receive the redirect axle 816 (FIGS. 10A-10B), and thus extend coaxially along the redirect pivot axis $R_1$. The rotation axis $P_5$ of each bushing 1106*a,b*, however, is non-collinear with (e.g., not parallel to, distinct from) the redirect pivot axis $R_1$, but instead extends at an angle offset therefrom. Consequently, in operation, each pulley 904*a,b* and 906*a,b* (FIGS. 9A-9B) rotates on the corresponding pulley support 908*a,b* about the rotation axis $P_5$, which is angled away from the redirect pivot axis $R_1$.

Referring again to FIGS. 10A and 10B, the first redirect pulleys 812 are each rotatably mounted to the first pulley support 908*a*, and the second redirect pulleys 814 are each rotatably mounted to the second pulley support 908*b*, and the redirect axle 816 extends uninterrupted through the entire assembly. More specifically, the first low force redirect pulley 904*a* is rotatably mounted to the first bushing 1106*a* provided on one side of the substrate 1102 of the first support pulley 908*a*, and the first high force redirect pulley 906*a* is rotatably mounted to the second bushing 1106*b* provided on the opposite side of the substrate 1102 of the first support pulley 908*a*. Similarly, the second low force redirect pulley 904*b* is rotatably mounted to the first bushing 1106*a* provided on one side of the substrate 1102 of the second support pulley 908*b*, and the first high force redirect pulley 906*b* is rotatably mounted to the second bushing 1106*b* provided in the opposite side of the substrate 1102 of the second support pulley 908*b*. The first low force and high force redirect pulleys 904*a*, 906*a* are mounted to the first pulley support 908*a* such that they rotate in parallel planes, and the second low force and high force redirect pulleys 904*b*, 906*b* are mounted to the second pulley support 908*b* such that they rotate in parallel planes.

Figures 12A, 12B:
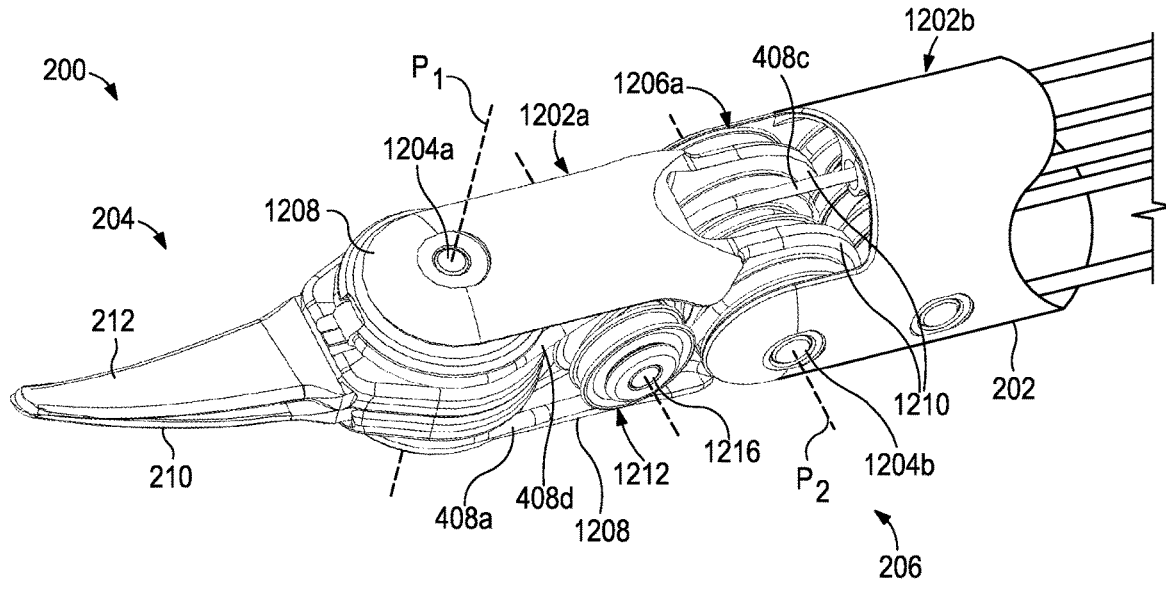
FIGS. 12A and 12B are enlarged, isometric views of another example of the distal end of the surgical tool of FIG. 2, according to one or more additional embodiments.

FIGS. 12A and 12B are enlarged, isometric views of another example of the distal end of the surgical tool 200, according to one or more additional embodiments. More specifically, FIGS. 12A-12B are enlarged left and right isometric views of alternative examples of the end effector 204 and the wrist 206. The embodiment shown in FIGS. 12A-12B may be substantially similar to the embodiment of FIGS. 8A-8B, and therefore may be best understood with reference thereto, where like numerals will represent like components not described again in detail. The end effector 204 in FIGS. 12A-12B, however, comprises surgical scissors, where the first and second blades 210, 212 are opposing scissor blades as compared to the needle driver of FIGS. 8A-8B.

As illustrated, the wrist 206 operatively couples the end effector 204 to the shaft 202 (or a shaft adapter interposing the distal end of the shaft 202 and the wrist 206). Moreover, the wrist 206 includes a distal clevis 1202*a* and a proximal clevis 1202*b*. The jaws 210, 212 are rotatably mounted to the distal clevis 1202*a* at a first axle 1204*a*, the distal clevis 1202*a* is rotatably mounted to the proximal clevis 1202*b* at a second axle 1204*b*, and the proximal clevis 1202*b* is operatively coupled to the distal end 406 of the shaft 202. The first pivot axis $P_1$ extends through the first axle 1204*a* and the second pivot axis $P_2$ extends through the second axle 1204*b*.

The drive cables 408*a-d* pass through the wrist 206 and are operatively coupled to the end effector 204. In the illustrated embodiment, the drive cables pass 408*a-d* through at least a first set of pulleys 1206*a* before reaching the end effector 204. The first set of pulleys 1206*a* is rotatably mounted to the proximal clevis 1202*b* at the second axle 1204*b*. The first and second drive cables 408*a,b* are coupled to (terminate at) the first jaw 210, and the third and fourth drive cables 408*c,d* are coupled to (terminate at) the second jaw 212.

As illustrated, the distal clevis 1202*a* includes first and second distally extending arms 1208, and the jaws 210, 212 are arranged between (interpose) the distally extending arms 1208 in a gap defined between the arms 1208. Each end of the first axle 1204*a* extends through or is otherwise mounted to a corresponding one of the distally extending arms 1208, and the jaws 210, 212 are rotatably mounted to the first axle 1204.

The distal clevis 1202*a* further includes first and second proximally extending arms 1210 that extend in the opposite direction as the distally extending arms 1208. In the illustrated embodiment, the distally extending arms 1208 extend in corresponding horizontal, parallel planes, and the proximally extending arms 1210 extend in corresponding vertical, parallel planes, where the vertical and horizontal planes are 90° offset from each other. The first set of pulleys 1206*a* is rotatably mounted to the proximally extending arms 1210 at the second axle 1204*b*, which extends through corresponding apertures (not shown) defined in the proximally extending arms 1210.

The wrist 206 further includes one or more first redirect pulleys 1212 (FIG. 12A) and one or more second redirect pulleys 1214 (FIG. 12B). In the illustrated embodiment, there are two first redirect pulleys 1212 and two second redirect pulleys 1214, but only one first or second redirect pulley 1212, 1214 may be included. The redirect pulleys 1212, 1214 may be rotatably mounted to the distal clevis 1202a and arranged to axially interpose the first set of pulleys 1206a and the jaws 210, 212. The first redirect pulleys 1212 may be configured to receive the first and fourth drive cables 408a,d from the first set of pulleys 1206a and redirect the drive cables 408a,d to the first and second jaws 210, 212, respectively. Similarly, the second redirect pulleys 1214 may be configured to receive the second and third drive cables 408b,c from the first set of pulleys 1206a and redirect the drive cables 408b,c to the second and first jaws 212, 210 respectively. Redirecting the drive cables 408a-d from the first set of pulleys 1206a to the jaws 210, 212 using the redirect pulleys 1212, 1214 helps reduce or entirely eliminate the fleet angle of the drive cables 408a-d as they are received by the first and second jaws 210, 212.

In the illustrated embodiment, the redirect pulleys 1212, 1214 are mounted to first and second pulley supports (not fully visible), respectively, which are mounted to the distal clevis 1202a. In some embodiments, the first and second pulley supports may be mounted to the distal clevis 1202a at a redirect axle 1216 that extends uninterrupted between lateral sides of the distal clevis 1202a. A redirect pivot axis $R_1$ extends through the redirect axle 1216 and may be angularly offset from each of the longitudinal axis $A_2$ of the end effector 204, the first pivot axis $P_1$, and the second pivot axis $P_2$, but the redirect pivot axis $R_1$ may extend in a plane that is parallel to a plane through which the second pivot axis $P_2$ extends. In some embodiments, for example, the redirect pivot axis $R_1$ may be angularly offset from the first pivot axis $P_1$ by around 45° and simultaneously angularly offset from the second pivot axis $P_2$ by around 45°. In other embodiments, however, the first and second redirect axes $R_1$, $R_2$ may be angularly offset from the first and second pivot axes $P_1$, $P_2$ by more or less than 45°, without departing from the scope of the disclosure. As described in more detail below, the first and second redirect pulleys 1212, 1214 are rotatably mounted to the first and second pulley supports, respectively, but are mounted such that their axis of rotation is angularly offset from and non-parallel to the redirect pivot axis $R_1$.

Figure 13A:
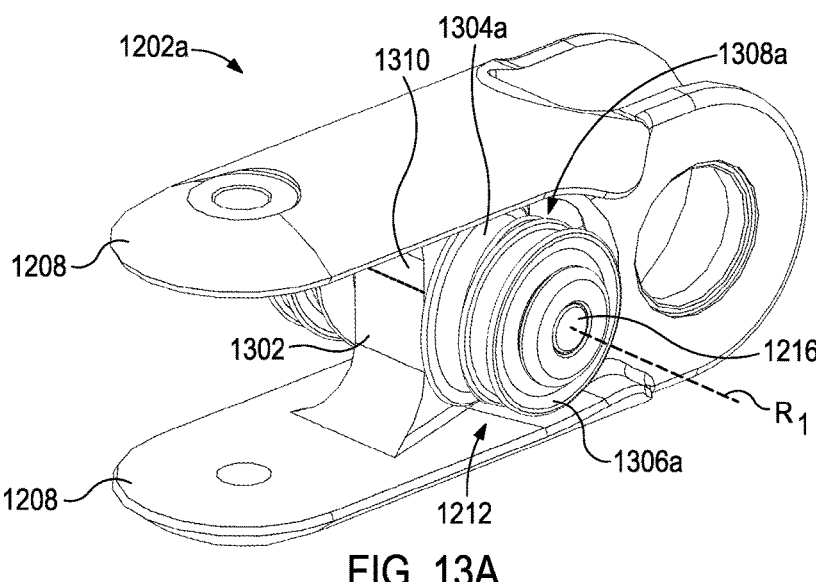
FIGS. 13A and 13B are isometric right and left views, respectively, of the distal clevis and the first and second redirect pulleys of FIGS. 12A-12B, according to one or more embodiments.
Figure 13B:
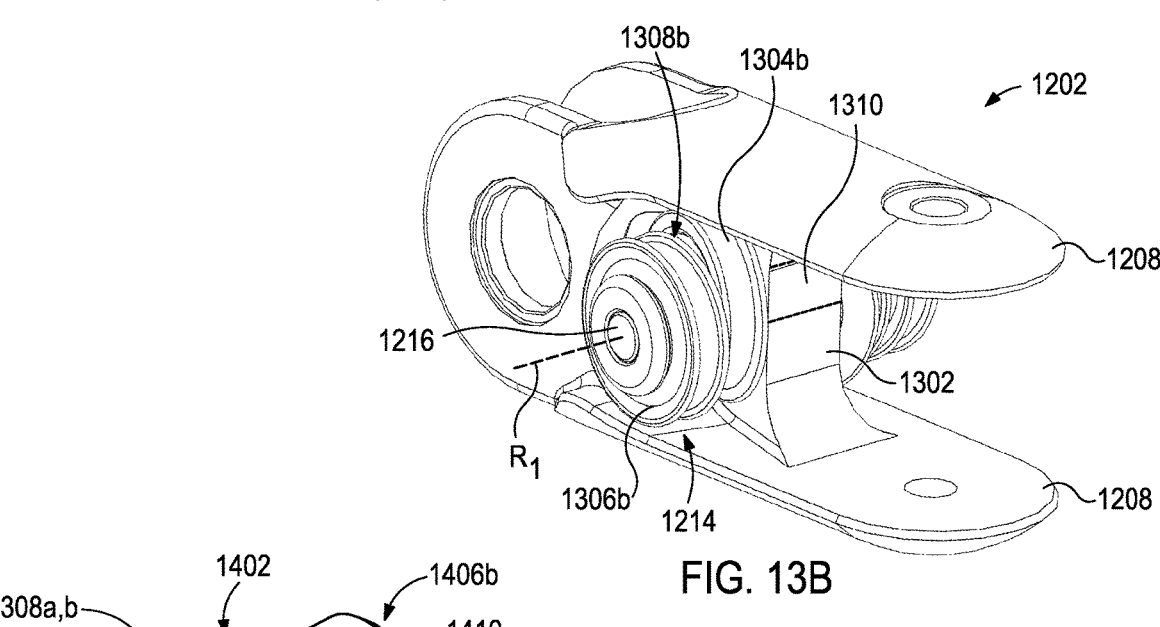

FIGS. 13A and 13B are isometric right and left views, respectively, of the distal clevis 1202a and the first and second redirect pulleys 1212, 1214 mounted thereto, according to one or more embodiments. In some embodiments, as illustrated, the distal clevis 1202a may provide a central support 1302 extending vertically between the distally extending arms 1208, and the first redirect pulleys 1212 may be mounted on one side of the central support 1302, and the second redirect pulleys 1214 may be mounted on the opposite side of the central support 1302.

In the illustrated embodiment, the first redirect pulleys 1212 include a first low force redirect pulley 1304a and a first high force redirect pulley 1306a, and the second redirect pulleys 1214 include a second low force redirect pulley 1304b and a second high force redirect pulley 1306b. The first and second low force redirect pulleys 1304a,b may be configured to redirect the open cables 408b,d (FIGS. 12A-12B) to the jaws 210, 212 (FIGS. 12A-12B), and the first and second high force redirect pulleys 1306a,b may be configured to redirect the closure cables 408a,c (FIGS. 12A-12B) to the jaws 210, 212.

The first redirect pulleys 1212 (i.e., the first low force and high force redirect pulleys 1304a, 1306a) are each rotatably mounted to a first pulley support 1308a (mostly occluded), and the second redirect pulleys 1214 (i.e., the second low force and high force redirect pulleys 1304b, 1306b) are each rotatably mounted to a second pulley support 1308b (mostly occluded). The first and second pulley supports 1308a,b are mounted to the redirect axle 1216 that extends through the distal clevis 1202a along the redirect pivot axis $R_1$. In particular, the central support 1302 may define a central aperture 1310 (shown in dashed lines) through which the redirect axle 1216 extends, and the first and second pulley supports 1308a,b may be mounted to opposing ends of the redirect axle 1216. The first and second redirect pulleys 1212, 1214 are rotatably mounted to the first and second pulley supports 1308a,b, respectively, but at least one of the pulleys 1212, 1214 rotates about an axis that is non-collinear with (e.g., non-parallel to, angularly offset from, distinct, etc.) the redirect pivot axis $R_1$.

Figure 14:
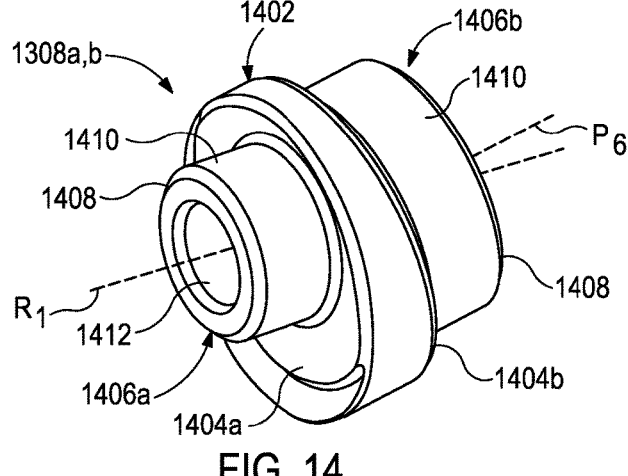
FIG. 14 is an isometric view of an example pulley support, according to one or more embodiments.

Referring briefly to FIG. 14, illustrated is an isometric view of an example pulley support 1308a,b, according to one or more embodiments. The pulley support shown in FIG. 14 represents either pulley support 1308a,b, which are substantially identical. As illustrated, the pulley support 1308a,b provides a substrate 1402 having opposing front and back faces 1404a and 1404b. A first bushing 1406a extends from or is otherwise provided on the front face 1404a and extends away from the substrate 1402, and a second bushing 1406b extends from or is otherwise provided on the back face 1404b and extends away from the substrate 1402. In the illustrated embodiment, the substrate 1402 exhibits a wedge shape. Consequently, the first and second bushings 1406a,b extend from the front and back faces 1404a,b at different angles and otherwise not parallel to each other.

Each bushing 1406a,b provides a generally cylindrical body 1408 having a circular cross-section and a smooth and circular side wall 1410. The low and high force pulleys 1304a,b and 1306a,b (FIGS. 9A-9B) may be configured to be rotatably mounted to the pulley supports 1308a,b on the corresponding side walls 1410. Each bushing 1406a,b allows the corresponding pulley 1304a,b and 1306a,b to rotate on the corresponding pulley support 1308a,b.

As illustrated, the pulley support 1308a, b includes a support aperture 1412 defined coaxially through the opposing bushings 1406a,b. The support aperture 1412 is configured to receive the redirect axle 1216 (FIGS. 13A-13B), and thus extend coaxially along the redirect pivot axis $R_1$. In some embodiments, the support aperture 1412 extends through the entire pulley support 1308a,b and the redirect axle 1216 extends uninterrupted through the pulley support 1308a,b. In other embodiments, however, the support aperture 1412 extends only partially through the pulley support 1308a,b. In such embodiments, the redirect axle 1216 may terminate at a location within the interior of the pulley support 1308a,b.

Because of the wedge-shape of the substrate 1402, at least one of the bushings 1406a,b will exhibit a rotation axis $P_6$ that is non-collinear with (e.g., non-parallel, angularly offset from, distinct from, etc.) the redirect pivot axis $R_1$. In the illustrated embodiment, the second bushing 1406b extends from the substrate 1402 along the rotation axis $P_6$, and the pulley rotatably mounted thereto will similarly rotate about the rotation axis $P_6$, thus rotating at an angle offset from the redirect pivot axis $R_1$. In some embodiments, as illustrated, the first bushing 1406a may share an axis with the redirect pivot axis $R_1$ such that the pulley rotatably mounted thereto will rotate about the redirect pivot axis $R_1$. Moreover, in some embodiments, as illustrated, the first and second bushings 1406a,b may exhibit dissimilar diameters, but could alternatively exhibit similar diameters.

Referring again to FIGS. 13A and 13B, with continued reference to FIG. 14, the first redirect pulleys 1212 are each rotatably mounted to the first pulley support 1308a, and the second redirect pulleys 1214 are each rotatably mounted to the second pulley support 1308b, and the redirect axle 1216 may extend through the entire assembly. More specifically, the first low force redirect pulley 1304a is rotatably mounted to the second bushing 1406b provided on one side of the substrate 1402 of the first support pulley 1308a, and the first high force redirect pulley 1306a is rotatably mounted to the first bushing 1406a provided on the opposite side of the substrate 1402 of the first support pulley 1308a. Similarly, the second low force redirect pulley 1304b is rotatably mounted to the second bushing 1406b provided on one side of the substrate 1402 of the second support pulley 1308b, and the first high force redirect pulley 1306b is rotatably mounted to the first bushing 1406a provided in the opposite side of the substrate 1402 of the second support pulley 1308b. The first low force and high force redirect pulleys 1304a, 1306a are mounted to the first pulley support 1308a such that they rotate in non-parallel planes, and the second low force and high force redirect pulleys 1304b, 1306b are mounted to the second pulley support 1308b such that they rotate in non-parallel planes.

Figure 15:
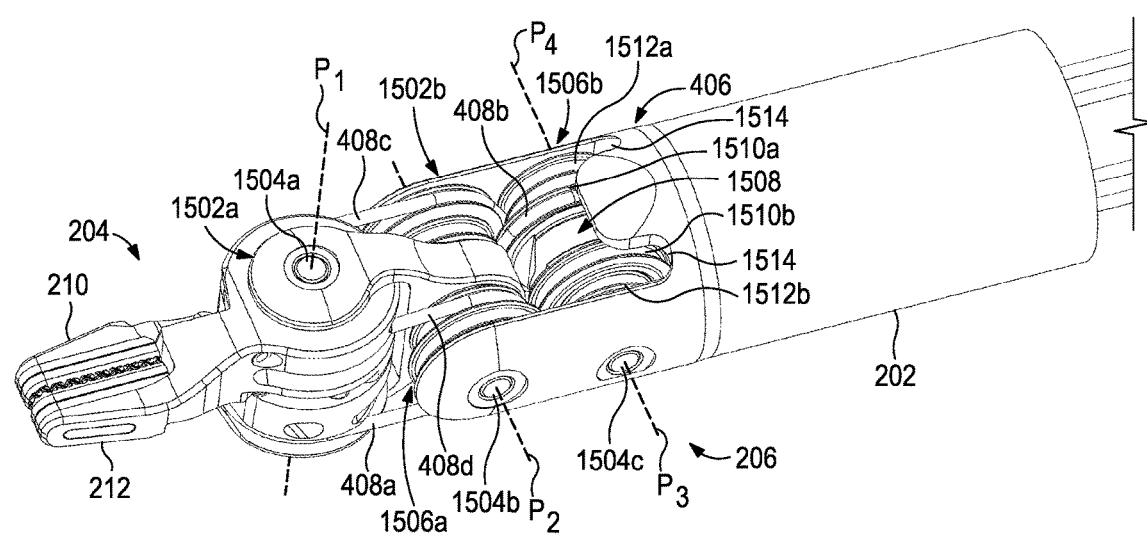
FIG. 15 is an enlarged, isometric view of another example of the distal end of the surgical tool of FIG. 2, according to one or more additional embodiments.

FIG. 15 is an enlarged, isometric view of another example of the distal end of the surgical tool 200, according to one or more additional embodiments. More specifically, FIG. 15 is an enlarged view of alternative examples of the end effector 204 and the wrist 206. The embodiment shown in FIG. 15 may be substantially similar to the embodiment of FIGS. 4A-4B, and therefore may be best understood with reference thereto, where like numerals will represent like components not described again in detail. The wrist 206 operatively couples the end effector 204 to the shaft 202 (or a shaft adapter interposing the distal end of the shaft 202 and the wrist 206), and includes a distal clevis 1502a and a proximal clevis 1502b. The jaws 210, 212 are rotatably mounted to the distal clevis 1502a at a first axle 1504a, the distal clevis 1502a is rotatably mounted to the proximal clevis 1502b at a second axle 1504b, and the proximal clevis 1502b is operatively coupled to the distal end 406 of the shaft 202.

The wrist 206 provides the first pivot axis $P_1$ that extends through the first axle 1504a and the second pivot axis $P_2$ that extends through the second axle 1504b. Moreover, the drive cables 408a-d extend longitudinally through the wrist 206 to be operatively coupled to the end effector 204. The first and second drive cables 408a,b are coupled to (terminate at) the first jaw 210, and the third and fourth drive cables 408c,d are coupled to (terminate at) the second jaw 212.

The wrist 206 includes a first set of pulleys 1506a and a second set of pulleys 1506b, each configured to interact with and redirect the drive cables 408a-d as they pass through the wrist 206. The first set of pulleys 1506a is rotatably mounted to the proximal clevis 1502b at the second axle 1504b and the second set of pulleys 1506b is also rotatably mounted to the proximal clevis 1502b but at third and fourth axles 1504c and 1504d (only axle 1504c visible) located proximal to the second axle 1504b. A third pivot axis $P_3$ extends through the third axle 1504c, and a fourth pivot axis $P_4$ extends through the fourth axle 1504d, and each pivot axis $P_3$, $P_4$ is parallel to the second pivot axis $P_2$ but eccentric (not coaxial) with each other.

In the illustrated embodiment, the surgical tool 200 further includes a pulley support 1508 to which the second set of pulleys 1506b is mounted. The pulley support 1508 is mounted to the proximal clevis 1502b at the third and fourth axles 1504c,d (only axle 1504c visible). First and second "low force" pulleys 1510a and 1510b, and first and second "high force" pulleys 1512a and 1512b may be mounted to the pulley support 1508 to receive and reroute the drive cables 408a-d within the wrist 206. The configuration and geometry of the pulley support 1508 shifts the axes of rotation of the low force pulleys 1510a,b to be eccentric to the third and fourth pivot axes $P_3$, $P_4$, respectively. This also allows the size (e.g., diameter) of each high force pulley 1512a,b to be increased, which increases the life of the open cables 408b,d by reducing the bending stress of the cable material.

In some embodiments, to accommodate for the increased size of the high force pulleys 1512a,b, the proximal clevis 1502b may define reliefs or slots 1514 laterally aligned with the high force pulleys 1512a,b. In at least one embodiment, for example, one or both of the high force pulleys 1512a,b may extend laterally outward and into the adjacent slot 1514.

Figure 16:
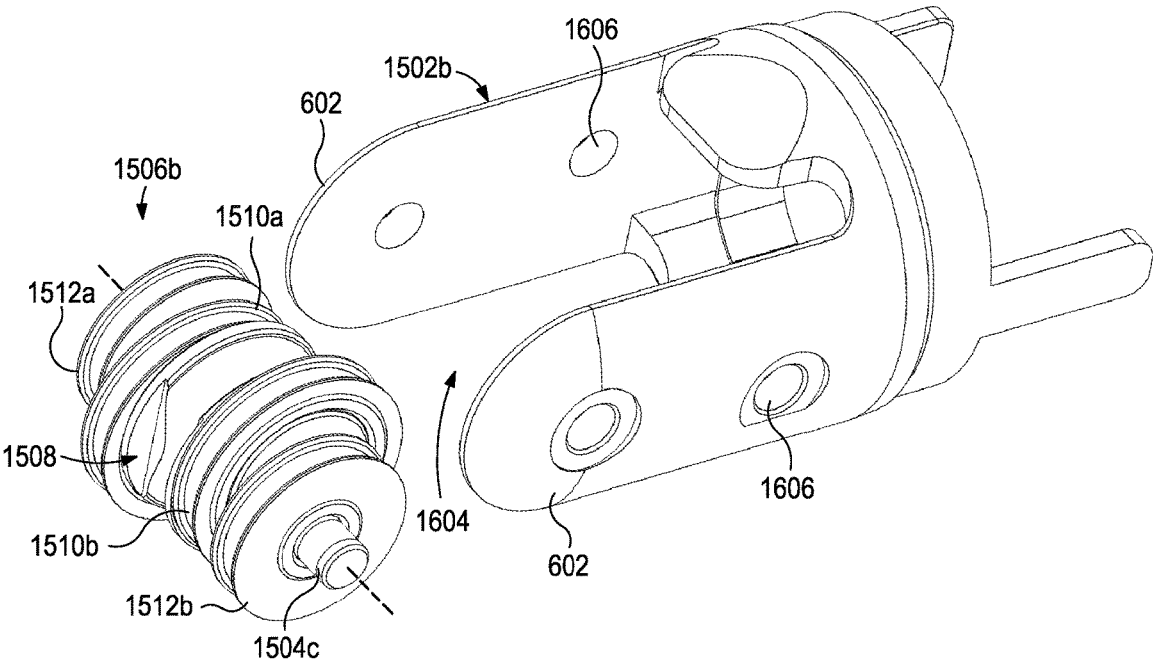
FIG. 16 is a partially exploded isometric view of the proximal clevis and the second set of pulleys of FIG. 15, according to one or more embodiments.

FIG. 16 is a partially exploded isometric view of the proximal clevis 1502b and the second set of pulleys 1506b, according to one or more embodiments. In particular, the second set of pulleys 1506b is shown exploded from the proximal clevis 1502b to enable a more complete view of the assembly.

As illustrated, the proximal clevis 1502b includes first and second distally extending arms 602 that extend in corresponding parallel planes. A gap 1604 is provided between the arms 602 to accommodate the second set of pulleys 1506b. While not shown, the gap 1604 may also be configured to accommodate the first set of pulleys 1506a (FIG. 15). The second set of pulleys 1506b may mounted to the distally extending arms 602a via combination the pulley support 1508 and the third and fourth axles 1504c,d (only third axle 1504c visible). The third and fourth axles 1504c,d may be received within corresponding apertures 1606 defined in the proximal clevis 1502b and, more particularly, in the distally extending arms 602. In some embodiments, the third and fourth axles 1504c,d are welded on the outside of the proximal clevis 1502b at the corresponding apertures 1606.

As illustrated, the second set of pulleys 1506b includes the first and second inner or "low force" pulleys 1510a,b and first and second outer or "high force" pulleys 1512a,b. The high force pulleys 1512a,b are arranged at or near the opposing ends of the third and fourth axles 1504c,d, and the low force pulleys 1510a,b interpose the high force pulleys 1512a,b.

FIG. 17 is a partially exploded isometric view of the second set of pulleys 1506b, according to one or more embodiments. In particular, the low force and high force pulleys 1510a,b and 1512a,b are shown exploded from the pulley support 1508. As illustrated, the pulley support 1508 provides a substrate 1702 having opposing front and back faces 1704a and 1704b. In the illustrated embodiment, the substrate 1702 is substantially cylindrical and exhibits a circular cross-section. A first bushing 1706a extends from or is otherwise provided on the front face 1704a and extends away from the substrate 1702, and a second bushing 1706b extends from or is otherwise provided on the back face 1704b and extends away from the substrate 1702. As illustrated, each bushing 1706a,b provides a generally cylindrical body 1708 having a circular cross-section and a smooth and circular side wall 1710. The high force pulleys 1510a,b may be configured to be rotatably mounted to the first and second bushings 1706a,b, respectively, at the corresponding side walls 1710. Each bushing 1706a,b allows the corresponding pulley 1510a,b to rotate on the pulley support 1508 about a corresponding rotation axis $P_5$ or $P_6$, respectively, of the corresponding bushing 1706*a,b*. The rotation axes $P_5$, $P_6$ may extend parallel to each other, but are non-coaxial (e.g., eccentric).

As illustrated, each bushing 1706*a,b* defines a support aperture 1712*a* and 1712*b* (only aperture 1712*a* visible) configured to receive a corresponding one of the third and fourth axles 1504*c,d*. In particular, the third axle 1504*c* may be received within the support aperture 1712*a* defined in the first bushing 1706*a*, and the fourth axle 1504*d* may be received within the support aperture 1712*b* defined in the second bushing 1706*b*. Moreover, the low force pulleys 1512*a,b* may be configured to be rotatably mounted to the third and fourth axles 1504*c,d*, respectively. Each axle 1504*c,d* allows the corresponding pulley 1512*a,b* to rotate about the third or fourth pivot axis $P_3$, $P_4$, respectively. The pivot axes $P_3$, $P_4$ may extend parallel to each other, but are collinear (e.g., they are non-coaxial or eccentric). Moreover, the pivot axes $P_3$, $P_4$ may extend parallel to the rotation axes $P_5$, $P_6$, but may also be non-collinear (e.g., non-coaxial or eccentric) to the rotation axes $P_5$, $P_6$.

FIGS. 18A and 18B are exploded, isometric left and right views of the pulley support 1508 and the third and fourth axles 1504*c,d*, according to one or more embodiments. As illustrated, each bushing 1706*a,b* defines the corresponding support aperture 1712*a* and 1712*b*, where the third axle 1504*c* is receivable within the first support aperture 1712*a* defined in the first bushing 1706*a*, and the fourth axle 1504*d* is receivable within the second support aperture 1712*b* defined in the second bushing 1706*b*.

Figure 19:
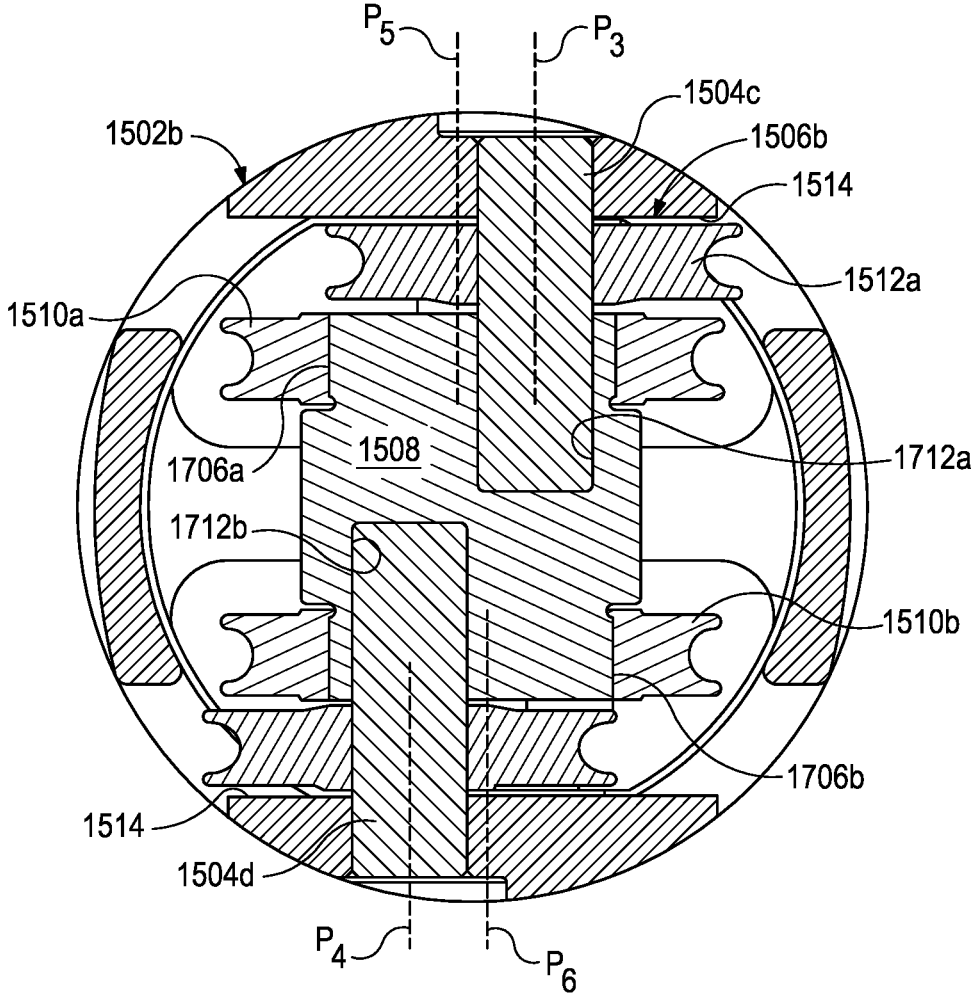
FIG. 19 is a cross-sectional side view of the second set of pulleys mounted to the proximal clevis of FIG. 15, according to one or more embodiments.

FIG. 19 is a cross-sectional side view of the second set of pulleys 1506*b* mounted to the proximal clevis 1502*b*, according to one or more embodiments. As illustrated, the high force pulleys 1510*a,b* are rotatably mounted to the first and second bushings 1706*a,b*, respectively, and the low force pulleys 1512*a,b* are rotatably mounted to the third and fourth axles 1504*c,d*, respectively, as received within corresponding support apertures 1712*a,b* defined in the pulley support 1508. Moreover, the low force pulleys 1512*a,b* are rotatable about the third or fourth pivot axis $P_3$, $P_4$, respectively, while the high force pulleys 1510*a,b* are rotatable about the corresponding rotation axis $P_5$ or $P_6$, respectively, of the corresponding bushing 1706*a,b*. The rotation axes $P_5$, $P_6$ may extend parallel to each other, but are non-collinear (eccentric or distinct). The pivot axes $P_3$, $P_4$ extend parallel to each other, but are non-collinear (eccentric or distinct). Moreover, the pivot axes $P_3$, $P_4$ also extend parallel to the rotation axes $P_5$, $P_6$, but are non-coaxial with (eccentric to) the rotation axes $P_5$, $P_6$.

The design and geometry of the pulley support 1508 may be advantageous in providing small diameter third and fourth axles 1504*c,d* for the high force pulleys 1510*a,b*, which helps reduce friction. The pulley support 1508 also provides a structural shift of the placement for the larger high force pulleys 1510*a,b*, where space within the wall thickness of the proximal clevis 1502*b* is used. As illustrated, the larger diameter high force pulleys 1510*a,b* may extend at least partially into the slots 1514 defined in the sidewall of the proximal clevis 1502*b*.

Embodiments Disclosed Herein Include

A. A surgical tool includes a drive housing having an elongate shaft extending therefrom, an end effector arranged at a distal end of the shaft and including opposing first and second jaws, and a wrist interposing the shaft and the end effector. The wrist includes a clevis, a pulley support mounted to the clevis at an axle having a pivot axis extending through the axle, and a pulley rotatably mounted to the pulley support and rotatable about a rotation axis that is non-collinear with the pivot axis. The surgical tool further includes a plurality of drive cables extending from the drive housing, wherein one of the plurality of drive cables is routed through the wrist and engages the pulley.

B. A surgical tool includes a drive housing having an elongate shaft extending therefrom, an end effector arranged at a distal end of the shaft and including opposing first and second jaws, and a wrist interposing the shaft and the end effector and including a clevis and a pulley support mounted to the clevis. The pulley support includes a substrate having opposing front and back faces, a first bushing provided on the front face, and a second bushing provided on the back face. The surgical tool further includes a first pulley rotatably mounted to the first bushing, a second pulley rotatably mounted to the second bushing, and a plurality of drive cables extending from the drive housing and including a first drive cable engageable with the first pulley and a second drive cable engageable with the second pulley.

Each of embodiments A and B may have one or more of the following additional elements in any combination: Element 1: wherein the clevis comprises a proximal clevis and the pulley comprises a first pulley, the wrist further including a distal clevis to which the first and second jaws are rotatably mounted, the proximal clevis also being rotatably coupled to the distal clevis and operatively coupled to the distal end of the shaft, and a set of pulleys mounted to the proximal clevis and including the first pulley, the set of pulleys further including a second pulley rotatably mounted to the axle and arranged laterally inward from the first pulley, wherein the rotation axis is parallel but eccentric to the pivot axis such that the first pulley rotates on the pulley support eccentric to the second pulley. Element 2: wherein the pulley support comprises a cylindrical body having a circular cross-section and providing opposing front and back faces, and a side wall extending between the front and back faces, the first pulley being rotatably mounted on the side wall, a support aperture defined through the cylindrical body along the pivot axis and through which the axle extends, and a cylindrical axle boss extending laterally outward from the front face eccentric to the pivot axis and receivable within a corresponding boss aperture defined in the proximal clevis. Element 3: wherein a slot is defined in the proximal clevis and a portion of the first pulley extends into the slot. Element 4: wherein the pulley comprises a redirect pulley, the pivot axis comprises a redirect pivot axis, and the axle comprises a redirect axle, the pulley support comprising a substrate having opposing front and back faces, a bushing provided on the front face and extending away from the substrate, the redirect pulley being rotatably mounted to the bushing about the rotation axis, and a support aperture defined through the bushing and extending along the redirect pivot axis to accommodate the redirect axle, wherein the rotation axis is non-parallel to the redirect pivot axis. Element 5: wherein the redirect pulley comprises a first redirect pulley, the bushing comprises a first bushing, and the rotation axis comprises a first rotation axis, the pulley support further comprising a second bushing provided on the back face and extending away from the substrate, and a second redirect pulley rotatably mounted to the second bushing and rotatable about a second rotation axis extending non-parallel to the redirect pivot axis, wherein the support aperture is defined through the first and second bushings and extends along the redirect pivot axis to receive the redirect axle, and wherein the substrate is planar such that the first rotation axis is parallel but eccentric to the second rotation axis, the first and second redirect pulleys rotating eccentric to each other in parallel planes. Element 6: wherein the clevis comprises a distal clevis and includes first and second proximally extending arms that extend in parallel planes, opposing redirect axle apertures defined in each proximally extending arm to receive opposing ends of the redirect axle, a central support interposing the first and second proximally extending arms and thereby defining a slot between the central support and one of the first and second proximally extending arms, the slot being sized to accommodate the pulley support and the first and second redirect pulleys, and a central aperture defined through the central support and extending along the redirect pivot axis to receive the redirect axle. Element 7: wherein the redirect pulley comprises a first redirect pulley, the bushing comprises a first bushing, and the rotation axis comprises a first rotation axis, the pulley support further comprising a second bushing provided on the back face and extending away from the substrate, and a second redirect pulley rotatably mounted to the second bushing and rotatable about a second rotation axis, wherein the support aperture is defined through at least the first bushing and extends along the redirect pivot axis to accommodate the redirect axle, and wherein the substrate is wedge-shaped such that the first rotation axis is non-parallel to the second rotation axis, and the first and second redirect pulleys rotate in non-parallel planes. Element 8: wherein clevis comprises a distal clevis and includes first and second distally extending arms that extend in parallel planes, and a central support extending between the first and second distally extending arms and defining a central aperture that extends along the redirect pivot axis to receive the redirect axle, wherein the pulley support and the first and second redirect pulleys are positioned on one side of the central support.

Element 9: wherein the first and second pulleys comprise first and second redirect pulleys, respectively, the wrist further including a redirect axle mounted to the clevis and having a redirect pivot axis extending through the redirect axle, the pulley support being mounted to the clevis at the redirect axle, and a support aperture defined through the first and second bushings and extending along the redirect pivot axis to receive the redirect axle, wherein the first pulley is rotatably mounted to the first bushing and rotatable about a first rotation axis that is non-collinear with the redirect pivot axis. Element 10: wherein the second redirect pulley is rotatably mounted to the second bushing and rotatable about a second rotation axis, and wherein the first rotation axis is parallel but eccentric to the second rotation axis such that the first and second redirect pulleys rotate eccentric to each other on the pulley support. Element 11: wherein the substrate is planar and the first and second redirect pulleys rotate in parallel planes. Element 12: wherein the clevis comprises a distal clevis and includes first and second proximally extending arms that extend in parallel planes, opposing redirect axle apertures defined in each proximally extending arm to receive opposing ends of the redirect axle, a central support interposing the first and second proximally extending arms and thereby defining a slot between the central support and one of the first and second proximally extending arms, the slot being sized to accommodate the pulley support and the first and second redirect pulleys, and a central aperture defined through the central support and extending along the redirect pivot axis to receive the redirect axle.

Element 13: wherein the second redirect pulley is rotatably mounted to the second bushing and rotatable about a second rotation axis, and wherein the substrate is wedge-shaped such that the first rotation axis is non-parallel to the second rotation axis, and the first and second redirect pulleys rotate in non-parallel planes. Element 14: wherein the clevis comprises a distal clevis and includes first and second distally extending arms that extend in parallel planes, and a central support extending between the first and second distally extending arms and defining a central aperture that extends along the redirect pivot axis to receive the redirect axle, wherein the pulley support and the first and second redirect pulleys are positioned on one side of the central support. Element 15: wherein the first pulley mounted to the first bushing rotates about a first rotation axis, and the second pulley mounted to the second bushing rotates about a second rotation axis, and wherein the first and second rotation axes are non-collinear but extend parallel to each other. Element 16: wherein the clevis includes first and second arms that extend in parallel planes, the wrist further including a first axle extending along a first pivot axis between a first support aperture defined in the first bushing and a first aperture defined in the first arm, a third pulley rotatably mounted to the first axle and rotatable about the first pivot axis, a second axle extending along a second pivot axis between a second support aperture defined in the second bushing and a second aperture defined in the second arm, and a fourth pulley rotatably mounted to the second axle and rotatable about the second pivot axis, wherein the first and second pivot axes are non-collinear but parallel to each other such that the third and fourth pulleys rotate eccentric to each other. Element 17: wherein the first and second rotation axes are non-collinear with but extend parallel to the first and second pivot axes. Element 18: wherein the first, second, third, and fourth pulleys each rotate in parallel planes.

By way of non-limiting example, exemplary combinations applicable to A and B include: Element 1 with Element 2; Element 1 with Element 3; Element 4 with Element 5; Element 5 with Element 6; Element 4 with Element 7; Element 7 with Element 8; Element 9 with Element 10; Element 10 with Element 11; Element 9 with Element 12; Element 9 with Element 13; Element 9 with Element 14; Element 15 with Element 16; Element 16 with Element 17; and Element 16 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, uphole, downhole and the like are used in relation to the illustrative embodiments as they are depicted in the figures, the upward direction being toward the top of the corresponding figure and the downward direction being toward the bottom of the corresponding figure.

What is claimed is the following:

1. A surgical tool, comprising:
an elongate shaft;
an end effector arranged at a distal end of the shaft and including opposing first and second jaws;
a wrist interposing the shaft and the end effector and including:
a clevis;
a pulley support mounted to the clevis at an axle having a pivot axis extending through the axle; and
a pulley defining an aperture to receive the pulley support to thereby rotatably mount the pulley to the pulley support, the pulley being rotatable relative to the pulley support about a rotation axis that is non-collinear with the pivot axis.

2. The surgical tool of claim 1, wherein the clevis comprises a proximal clevis and the pulley comprises a first pulley, the wrist further including:
a distal clevis to which the first and second jaws are rotatably mounted, the proximal clevis also being rotatably coupled to the distal clevis and operatively coupled to the distal end of the shaft; and
a set of pulleys mounted to the proximal clevis and including the first pulley, the set of pulleys further including a second pulley rotatably mounted to the axle and arranged laterally inward from the first pulley,
wherein the rotation axis is parallel but eccentric to the pivot axis such that the first pulley rotates on the pulley support eccentric to the second pulley.

3. The surgical tool of claim 2, wherein the pulley support comprises:
a cylindrical body having a circular cross-section and providing opposing front and back faces, and a side wall extending between the front and back faces, the first pulley being rotatably mounted on the side wall;
a support aperture defined through the cylindrical body along the pivot axis and through which the axle extends; and
a cylindrical axle boss extending laterally outward from the front face eccentric to the pivot axis and receivable within a corresponding boss aperture defined in the proximal clevis.

4. The surgical tool of claim 2, wherein a slot is defined in the proximal clevis and a portion of the first pulley extends into the slot.

5. The surgical tool of claim 1, wherein the pulley comprises a redirect pulley, the pivot axis comprises a redirect pivot axis, and the axle comprises a redirect axle, the pulley support comprising:
a substrate having opposing front and back faces;
a bushing provided on the front face and extending away from the substrate, the redirect pulley being rotatably mounted to the bushing about the rotation axis; and
a support aperture defined through the bushing and extending along the redirect pivot axis to accommodate the redirect axle,
wherein the rotation axis is non-parallel to the redirect pivot axis.

6. The surgical tool of claim 5, wherein the redirect pulley comprises a first redirect pulley, the bushing comprises a first bushing, and the rotation axis comprises a first rotation axis, the pulley support further comprising:
a second bushing provided on the back face and extending away from the substrate; and
a second redirect pulley rotatably mounted to the second bushing and rotatable about a second rotation axis extending non-parallel to the redirect pivot axis,
wherein the support aperture is defined through the first and second bushings and extends along the redirect pivot axis to receive the redirect axle, and
wherein the substrate is planar such that the first rotation axis is parallel but eccentric to the second rotation axis, the first and second redirect pulleys rotating eccentric to each other in parallel planes.

7. The surgical tool of claim 6, wherein the clevis comprises a distal clevis and includes:
first and second proximally extending arms that extend in parallel planes;
opposing redirect axle apertures defined in each of the proximally extending arms to receive opposing ends of the redirect axle;
a central support interposing the first and second proximally extending arms and thereby defining a slot between the central support and one of the first and second proximally extending arms, the slot being sized to accommodate the pulley support and the first and second redirect pulleys; and
a central aperture defined through the central support and extending along the redirect pivot axis to receive the redirect axle.

8. The surgical tool of claim 5, wherein the redirect pulley comprises a first redirect pulley, the bushing comprises a first bushing, and the rotation axis comprises a first rotation axis, the pulley support further comprising:
a second bushing provided on the back face and extending away from the substrate; and
a second redirect pulley rotatably mounted to the second bushing and rotatable about a second rotation axis, wherein the support aperture is defined through at least the first bushing and extends along the redirect pivot axis to accommodate the redirect axle, and wherein the substrate is wedge-shaped such that the first rotation axis is non-parallel to the second rotation axis, and the first and second redirect pulleys rotate in non-parallel planes.

9. The surgical tool of claim 8, wherein the clevis comprises a distal clevis and includes:

first and second distally extending arms that extend in parallel planes; and a central support extending between the first and second distally extending arms and defining a central aperture that extends along the redirect pivot axis to receive the redirect axle, wherein the pulley support and the first and second redirect pulleys are positioned on one side of the central support.

10. A surgical tool, comprising:

an elongate shaft extending therefrom;

an end effector arranged at a distal end of the shaft and including opposing first and second jaws;

a wrist interposing the shaft and the end effector and including a clevis and a pulley support mounted to the clevis, the pulley support including:

a substrate having opposing front and back faces;

a first bushing provided on the front face and defining a first support aperture portion; and a second bushing provided on the back face and defining a second support aperture portion;

a first pulley rotatably mounted to the first bushing and rotatable about a first rotation axis; and a second pulley rotatably mounted to the second bushing and rotatable about a second rotation axis that is non-collinear with the first rotation axis.

11. The surgical tool of claim 10, wherein the first and second pulleys comprise first and second redirect pulleys, respectively, the wrist further including:

a redirect axle mounted to the clevis and having a redirect pivot axis extending through the redirect axle, the pulley support being mounted to the clevis at the redirect axle;

wherein the first and second support aperture portions define a support aperture through the first and second bushings to receive the redirect axle, and wherein the first rotation axis is non-collinear with the redirect pivot axis.

12. The surgical tool of claim 11, wherein the first rotation axis is parallel but eccentric to the second rotation axis such that the first and second redirect pulleys rotate eccentric to each other on the pulley support.

13. The surgical tool of claim 12, wherein the substrate is planar and the first and second redirect pulleys rotate in parallel planes.

14. The surgical tool of claim 11, wherein the clevis comprises a distal clevis and includes:

first and second proximally extending arms that extend in parallel planes;

opposing redirect axle apertures defined in each of the proximally extending arms to receive opposing ends of the redirect axle;

a central support interposing the first and second proximally extending arms and thereby defining a slot between the central support and one of the first and second proximally extending arms, the slot being sized to accommodate the pulley support and the first and second redirect pulleys; and a central aperture defined through the central support and extending along the redirect pivot axis to receive the redirect axle.

15. The surgical tool of claim 11, wherein the second redirect pulley is rotatably mounted to the second bushing and rotatable about the second rotation axis, and wherein the substrate is wedge-shaped such that the first rotation axis is non-parallel to the second rotation axis, and the first and second redirect pulleys rotate in non-parallel planes.

16. The surgical tool of claim 11, wherein the clevis comprises a distal clevis and includes:

first and second distally extending arms that extend in parallel planes; and a central support extending between the first and second distally extending arms and defining a central aperture that extends along the redirect pivot axis to receive the redirect axle, wherein the pulley support and the first and second redirect pulleys are positioned on one side of the central support.

17. The surgical tool of claim 10, wherein the first and second rotation axes are parallel to each other.

18. The surgical tool of claim 17, wherein the clevis includes first and second arms that extend in parallel planes, the wrist further including:

a first axle extending along a first pivot axis between the first support aperture portion and a first aperture defined in the first arm;

a third pulley rotatably mounted to the first axle and rotatable about the first pivot axis;

a second axle extending along a second pivot axis between the second support aperture portion and a second aperture defined in the second arm; and a fourth pulley rotatably mounted to the second axle and rotatable about the second pivot axis, wherein the first and second pivot axes are non-collinear but parallel to each other such that the third and fourth pulleys rotate eccentric to each other.

19. The surgical tool of claim 18, wherein the first and second rotation axes are non-collinear with but extend parallel to the first and second pivot axes.

20. A surgical tool, comprising:

an elongate shaft;

an end effector including opposing first and second jaws; and a wrist interposing the shaft and the end effector and including:

a clevis defining a first aperture and a second aperture;

a pulley support defining a pulley support aperture and providing an axle boss extending into the first aperture;

an axle extending through the pulley support aperture and into the second aperture, wherein the axle defines a first axis; and a pulley mounted to the pulley support and being rotatable about a second axis that is non-collinear with the first axis.

* * * * *